US010577428B2

(12) United States Patent
Gruber et al.

(10) Patent No.: US 10,577,428 B2
(45) Date of Patent: *Mar. 3, 2020

(54) ANTI-FACTOR XI MONOCLONAL ANTIBODIES AND METHODS OF USE THEREOF

(71) Applicants: Oregon Health & Science University, Portland, OR (US); Vanderbilt University, Nashville, TN (US)

(72) Inventors: Andras Gruber, Portland, OR (US); Erik I. Tucker, Portland, OR (US); Stephen Raymond Hanson, Edmonds, WA (US); David Gailani, Franklin, TN (US)

(73) Assignees: Oregon Health & Science University, Portland, OR (US); Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,141

(22) Filed: Jul. 30, 2018

(65) Prior Publication Data

US 2018/0355057 A1 Dec. 13, 2018

Related U.S. Application Data

(60) Continuation of application No. 15/470,758, filed on Mar. 27, 2017, now abandoned, which is a continuation of application No. 14/809,551, filed on Jul. 27, 2015, now Pat. No. 9,636,399, which is a continuation of application No. 14/242,692, filed on Apr. 1, 2014, now Pat. No. 9,125,895, which is a continuation of application No. 13/783,952, filed on Mar. 4, 2013, now abandoned, which is a division of application No. 13/446,320, filed on Apr. 13, 2012, now Pat. No. 8,399,648, which is a division of application No. 12/744,037, filed as application No. PCT/US2008/084336 on Nov. 21, 2008, now Pat. No. 8,236,316.

(60) Provisional application No. 60/989,523, filed on Nov. 21, 2007.

(51) Int. Cl.
| *A61K 39/395* | (2006.01) |
| *C07K 16/36* | (2006.01) |
| *A61K 45/06* | (2006.01) |
| *A61K 39/00* | (2006.01) |

(52) U.S. Cl.
CPC .......... *C07K 16/36* (2013.01); *A61K 39/3955* (2013.01); *A61K 45/06* (2013.01); *A61K 2039/505* (2013.01); *C07K 2317/24* (2013.01); *C07K 2317/32* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/624* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,877,289 | A | 3/1999 | Thorpe et al. | |
| 6,989,250 | B2 | 1/2006 | Soderlind et al. | |
| 8,236,316 | B2 * | 8/2012 | Gruber | C07K 16/36 424/145.1 |
| 8,399,648 | B2 | 3/2013 | Gruber et al. | |
| 9,125,895 | B2 * | 9/2015 | Gruber | C07K 16/36 |
| 9,636,399 | B2 * | 5/2017 | Gruber | C07K 16/36 |

(Continued)

FOREIGN PATENT DOCUMENTS

| WO | WO 2006/055178 | 5/2006 |
| WO | WO 2008/133857 | 11/2008 |
| WO | WO 2009/154461 | 12/2009 |
| WO | WO 2010/065275 | 6/2010 |
| WO | WO 2011/149921 | 12/2011 |
| WO | WO 2011/161099 | 12/2011 |
| WO | WO 2012/004258 | 1/2012 |
| WO | WO 2012/028647 | 3/2012 |
| WO | WO 2012/143510 | 10/2012 |
| WO | WO 2012/152629 | 11/2012 |
| WO | WO 2013/030138 | 3/2013 |
| WO | WO 2013/030288 | 3/2013 |

OTHER PUBLICATIONS

Baglia et al., "Functional Domains in the Heavy-Chain Region of Factor XI: A High Molecular Weight Kininogen-Binding Site and a Substrate-Binding Site for Factor IX," *Blood* 74(1):244-251, 1989.

(Continued)

*Primary Examiner* — Michael Szperka
(74) *Attorney, Agent, or Firm* — Klarquist Sparkman LLP

(57) ABSTRACT

Compositions and methods for inhibiting thrombosis without compromising hemostasis are described. Compositions include anti-factor XI monoclonal antibodies (aXIMabs) capable of binding to an epitope on the heavy chain of human FXI, particularly the A3 domain of the heavy chain of human FXI. Compositions also include epitope-binding fragments, variants, and derivatives of the monoclonal antibodies, cell lines producing these antibody compositions, and isolated nucleic acid molecules encoding the amino acid sequences of the antibodies. The disclosure further includes pharmaceutical compositions comprising the disclosed anti-factor XI monoclonal antibodies, or epitope-binding fragments, variants, or derivatives thereof, in a pharmaceutically acceptable carrier. Methods of the disclosure include administering the compositions described above to a subject in need thereof for the purpose of inhibiting thrombosis, reducing a required dose of an antithrombotic agent in the treatment of thrombosis, treating metastatic cancer, or treating an acute inflammatory reaction.

19 Claims, 14 Drawing Sheets

Specification includes a Sequence Listing.

(56) References Cited

U.S. PATENT DOCUMENTS

| | | |
|---|---|---|
| 2005/0037006 A1* | 2/2005 | Barone .................. C07K 16/36 424/145.1 |
| 2006/0057140 A1 | 3/2006 | Feuerstein |
| 2008/0138837 A1 | 6/2008 | Greenfield et al. |
| 2015/0099298 A1 | 4/2015 | Wilmen et al. |
| 2017/0204195 A1 | 7/2017 | Gruber et al. |

OTHER PUBLICATIONS

Chothia et al. "Canonical structures for the hypervariable regions of immunoglobulins." *J Mol Bio* 196(4): 901-917, 1987.

Davie et al., "The Coagulation Cascade: Initiation, Maintenance, and Regulation," Biochemistry 30:10363-10370, 1991.

Davie et al., "Waterfall Sequence for Intrinsic Blood Clotting," *Science* 145:1310-1312, 1964.

De La Cadena et al., "Naturally Occurring Human Antibodies Against Two Distinct Functional Domains in the Heavy Chain of FXI/FXIa," *Blood* 72(5):1748-1754, 1988.

Fujikawa et al., "Amino Acid Sequence of Human Factor XI, a Blood Coagulation Factor with Four Tandem Repeats that are Highly Homologous with Plasma Prekallikrein," *Biochemistry* 25:2417-2424, 1986.

Gailani et al., "Factor XI Activation in a Revised Model of Blood Coagulation," *Science* 253:909-912, 1991.

Gruber et al., "Antithrombotic Factor XI Antibody Inhibition of the Intrinsic Pathway," *Blood* 98(11), Part 1:42a, abstract from the 43$^{rd}$ Annual Meeting of the American Society of Hematology, Orlando, FL, ISSN: 0006-4971, 2001.

Gruber et al., "Factor XI-Dependence of Surface- and Tissue Factor-Initiated Thrombus Propagation in Primates," *Blood* 102(3):953-955, 2003.

Gruber et al., "Relative antithrombotic and antihemostatic effects of protein C activator versus low-molecular-weight heparin in primates," *Blood* 109:3733-3740, 207.

Hanson et al. "Antithrombotic Effects of Thrombin-induced Activation of Endogenous Protein C in Primates," *J Clin Invest* 92:2003-2012, 1993.

Hoffman et al., "Rethinking the Coagulation Cascade," *Curr Hematol Rep* 4:391-396, 2005.

International Search Report and Written Opinion for PCT/US2008/084336, dated May 4, 2009, 10 pages.

Janeway et al., "Structure of the Molecule and Immunoglobulin Genes" in Immunobiology: The Immune System in Health and Disease, Ch. 3, pp. 3:1-3:11, 1997.

Johne et al., "Platelets promote coagulation factor XII-mediated proteolytic cascade systems in plasma," *Biol Chem* 387:173-178, 2006.

Kravtsov et al., "Factor XI contributes to thrombin generation in the absence of factor XII," *Blood* 114:452-458, 2009.

Kunik et al., "Structural consensus among antibodies defines the antigen binding site." *PLoS Comput Biol* 8(2): e1002388, 2012.

MacFarlane, "An Enzyme Cascade in the Blood Clotting Mechanism, and its Function as a Biochemical Amplifier," *Nature* 202:498-499, 1964.

Meijers et al., "High Levels of Coagulation Factor XI as a Risk Factor for Venous Thrombosis," *N Engl J Med* 342:696-701, 2000.

Paul, William E., "Immunogenicity and Antigen Structure," in *Fundamental Immunology*, Ch. 8, p. 242, 1993.

Payne et al., "Combined therapy with clopidogrel and aspirin significantly increases the bleeding time through a synergistic antiplatelet action," *J Vasc Surg* 35:1204-1209, 2002.

Portolano et al., "Lack of Promiscuity in Autoantigen-Specific H and L Chain Combinations as Revealed by Human H and L Chain Roulette," *J. Immunol.*, vol. 150:880-887, 1993.

Riva et al., "Loco-Regional Radioimmunotherapy of High-Grade Malignant Gliomas Using Specific Monoclonal Antibodies Labeled with 90Y: A Phase I Study," *Clin Cancer Res* 5(Suppl.):3275s-3280s, 1999.

Rosen et al., "The Factor of Facto XI Deficiency in Thyroid Neoplasia," *Surgery*, vol. 100:1062-1067, 1986.

Rudikoff et al., "Single Amino Acid Substitution Altering Antigen-Binding Specificity," *Proc. Natl. Acad. Sci. U.S.A.*, vol. 79:1979-1983, 1982.

Salomon et al., "Patients with severe factor XI deficiency have a reduced incidence of deep-vein thrombosis," *Thromb Haemost* 105:269-73, 2011.

Salomon et al., "Reduced incidence of ischemic stroke in patients with severe factor XI deficiency," *Blood* 111:4113-4117, 2008.

Smith et al., "The Prolonged Bleeding Time in Hemophilia A: Comparison of Two Measuring Technics in Clinical Associations," *Am J Clin Pathol* 83:211-215, 1985.

Sun et al., "Identification of a factor IX binding site on the third apple domain of activated factor XI." *J Biol Chem* 271(46): 29023-29028, 1996.

Sun et al., "Identification of Amino Acids in the Factor XI Apple 3 Domain Required for Activation of Factor IX," *J. Biol. Chem.* 274(51):36373-36378, 1999.

Tucker et al., "Inhibition of Factor XI Decreases Thrombin Production and Prevents Vascular Occlusion in Experimental Thrombosis in Primates," *Blood* 110(11): Part 1, p. 235A and 49$^{th}$ Annual Meeting of the American Society of Hematology, Dec. 8-11, 2007.

Tucker et al., "Prevention of Vascular Graft Occlusion and Thrombus-Associated Thrombin Generation by Inhibition of Factor XI," *Blood*, vol. 113:936-944, 2009.

Wu et al., "An analysis of the sequences of the variable regions of Bence Jones proteins and myeloma light chains and their implications for antibody complementarity." *J Exp Med* 132(2): 211-250, 1970.

Yamada et al., "Development of Antibody Against Epitope of Lipoprotein(a) Modified by Oxidation," *Circulation* 102:1639-1644, 2000.

\* cited by examiner ePTFE

60 µm

Collagen Coated

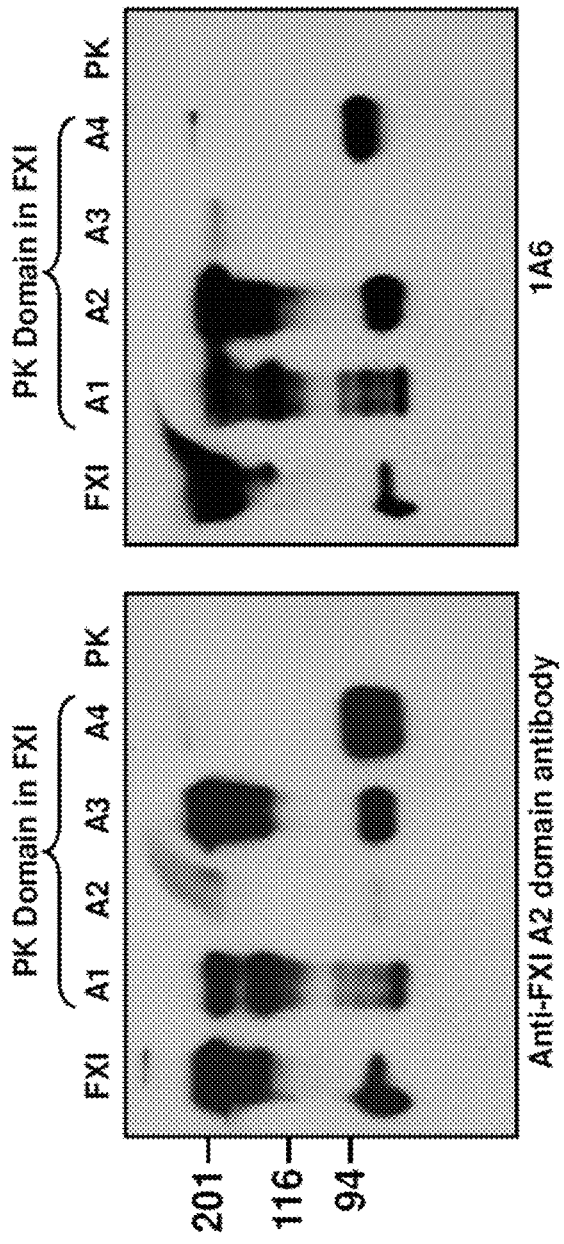
FIG. 9 Western blots of Factor XI, Prekallikrein, and FXI/PK Chimeras
(Antibody 1A6 Does not Recognize PK or FXI/PKA3)

FIG. 12

Factor XI Apple 3 Domain
Position of alanine substitutions which prevent
or reduce recognition by 1A6 in western blots

FIG. 13A

CAAGTTACTCTAAAAGAGTCTGGCCCTGGGATATTGAAGCCCTCACAGACCCTCAGTCTGACT
TGTTCTTTCTCTGGGTTTTCACTGAGCACTTCTGGTATGGGTGTAGGCTGGATTCGTCAGCCT
TCAGGGAAGGGTCTGGAGTGGCTGGCACACATTTGGTGGGATGATGATAAGTACTATAACC
CATCCCTGAAGAGCCAGCTCACAATCTCCAAGGATACCTCCAGAAACCAGGTTTTCCTCAAG
ATCACCAGTGTGGACGCTGCAGATACTGCCACTTACTACTGTGCTCGAAAGAGGTCTTCGGT
TGTAGCCCATTACTATGCTATGGACTACTGGGGTCAAGGAACCTCAGTCACCGTCTCCTCA
(SEQ ID NO:2)

QVTLKESGPGILKPSQTLSLTCSFSGFSLSTSGMGVGWIRQPSGKGLE
WLAHIWWDDDKYYNPSLKSQLTISKDTSRNQVFLKITSVDAADTATY
YCARKRSSVVAHYYAMDYWGQGTSVTVSS(SEQ ID NO:3)

FIG. 13B

GACATTGTGCTGACCCAATCTCCAGCTTCTTTGGCTGTGTCTCTAGGGCAGAGGGCCACCATCT
CCTGCAAGGCCAGCCAAAGTGTTGATTATGATGGTGATAGTTATCTGAACTGGTACCAAC
AGAAACCAGGACAGCCACCCAAACTCCTCATCTATGCTGCATCCAATCTAGAATCTGGGATC
CCAGCCAGGTTTAGTGGCAGTGGGTCTGGGACAGACTTCACCCTCAACATCCATCCTGTGGAG
GAGGAGGATGCTGCAACCTATTACTGTCAGCAAAGTAATGGGGATCCGTGG
ACGTTCGGTGGAGGCACCAAGCTGGAAATCAAA (SEQ ID NO:4)

DIVLTQSPASLAVSLGQRATISCKASQSVDYDGDSYLNWYQQKPGQP
PKLLIYAASNLESGIPARFSGSGSGTDFTLNIHPVEEDAATYYCQQSN
GDPWTFGGGTKLEIK(SEQ ID NO:5)

FIG. 13C

CAAGTTACTCTAAAAGAGTCTGGCCCTACCATAGTGAAGCCCACACAGACCCTCACTCTGACT
TGTTCTTTCTCTGGGTTTTCACTGAGCACTTCTGGTATGGGTGTAGGCTGGATTCGTCAGCCT
TCAGGGAAGGCTCTGGAGTGGCTGGCACACATTTGGTGGGATGATGATAAGTACTATAACC
CATCCCTGAAGAGCCGGCTCACAATCACCAAGGATACCTCCAAAAACCAGGTTGTCCTCACC
ATGACCAATATGGACGCTGTGGATACTGCCACTTACTACTGTGCTCGAAAGAGGTCTTCGGT
TGTAGCCCATTACTATGCTATGGACTACTGGGGTCAAGGAACCACAGTCACCGTCTCCTCA
(SEQ ID NO:6)

QVTLKESGPTIVKPTQTLTLTCSFSGFSLSTSGMGVGWIRQPSGKALE
WLAHIWWDDDKYYNPSLKSRLTITKDTSKNQVVLTMTNMDPVDTAT
YYCARKRSSVVAHYYAMDYWGQGTTVTVSS(SEQ ID NO:7)

FIG. 13D

GACATTGTGCTGACCCAATCTCCAGATTCTTTGGCTGTGTCTCTAGGGGAGAGGGCCACCATC
ACCTGCAAGGCCAGCCAAAGTGTTGATTATGATGGTGATAGTTATCTGAACTGGTACCAA
CAGAAACCAGGACAGCCACCCAAACTCCTCATCTATGCTGCATCCAATCTAGAATCTGGGAT
CCCAGACAGGTTTAGTGGCAGTGGGTCTGGGACAGACTTCACCCTCACCATCTCTTCTGTGCA
GGAGGAGGATGTGGCAACCTATTACTGTCAGCAAAGTAATGGGGATCCGTGG
ACGTTCGGTGGAGGCACCAAGGTGGAAATCAAA (SEQ ID NO:8)

DIVLTQSPDSLAVSLGERATINCKASQSVDYDGDSYLNWYQQKPGQP
PKLLIYAASNLESGIPDRFSGSGSGTDFTLTISSLQEEDVATYYCQQSN
GDPWTFGGGTKVEIK(SEQ ID NO:9)

SEQUENCE LISTING

<160> NUMBER OF SEQ ID NOS: 15

<210> SEQ ID NO 1
<211> LENGTH: 607
<212> TYPE: PRT
<213> ORGANISM: Homo sapiens

```
<400> SEQUENCE: 1

Glu Cys Val Thr Gln Leu Leu Lys Asp Thr Cys Phe Glu Gly Gly Asp
1               5                   10                  15

Ile Thr Thr Val Phe Thr Pro Ser Ala Lys Tyr Cys Gln Val Val Cys
            20                  25                  30

Thr Tyr His Pro Arg Cys Leu Leu Phe Thr Phe Thr Ala Glu Ser Pro
        35                  40                  45

Ser Glu Asp Pro Thr Arg Trp Phe Thr Cys Val Leu Lys Asp Ser Val
    50                  55                  60

Thr Glu Thr Leu Pro Arg Val Asn Arg Thr Ala Ala Tyr Ser Gly Tyr
65                  70                  75                  80

Ser Phe Lys Gln Cys Ser His Gln Ile Ser Ala Cys Asn Lys Asp Ile
                85                  90                  95

Tyr Val Asp Leu Asp Met Lys Gly Ile Asn Tyr Asn Ser Ser Val Ala
                100                 105                 110

Lys Ser Ala Gln Glu Cys Gln Glu Arg Cys Thr Asp Asp Val His Cys
            115                 120                 125

His Phe Phe Thr Tyr Ala Thr Arg Gln Phe Pro Ser Leu Glu His Arg
        130                 135                 140

Asn Ile Cys Leu Leu Lys His Thr Gln Thr Gly Thr Pro Thr Arg Ile
145                 150                 155                 160

Thr Lys Leu Asp Lys Val Val Ser Gly Phe Ser Leu Lys Ser Cys Ala
                165                 170                 175

Leu Ser Asn Leu Ala Cys Ile Arg Asp Ile Phe Pro Asn Thr Val Phe
                180                 185                 190

Ala Asp Ser Asn Ile Asp Ser Val Met Ala Pro Asp Ala Phe Val Cys
            195                 200                 205

Gly Arg Ile Cys Thr His His Pro Gly Cys Leu Phe Phe Thr Phe Phe
210                 215                 220

Ser Gln Glu Trp Pro Lys Glu Ser Gln Arg Asn Leu Cys Leu Leu Lys
225                 230                 235                 240

Thr Ser Glu Ser Gly Leu Pro Ser Thr Arg Ile Lys Lys Ser Lys Ala
            245                 250                 255

Leu Ser Gly Phe Ser Leu Gln Ser Cys Arg His Ser Ile Pro Val Phe
                260                 265                 270

Cys His Ser Ser Phe Tyr His Asp Thr Asp Phe Leu Gly Glu Glu Leu
            275                 280                 285

Asp Ile Val Ala Ala Lys Ser His Glu Ala Cys Gln Lys Leu Cys Thr
        290                 295                 300

Asn Ala Val Arg Cys Gln Phe Phe Thr Tyr Thr Pro Ala Gln Ala Ser
305                 310                 315                 320

Cys Asn Glu Gly Lys Gly Lys Cys Tyr Leu Lys Leu Ser Ser Asn Gly
                325                 330                 335

Ser Pro Thr Lys Ile Leu His Gly Arg Gly Gly Ile Ser Gly Tyr Thr
            340                 345                 350

Leu Arg Leu Cys Lys Met Asp Asn Glu Cys Thr Thr Lys Ile Lys Pro
        355                 360                 365

Arg Ile Val Gly Gly Thr Ala Ser Val Arg Gly Glu Trp Pro Trp Gln
        370                 375                 380

Val Thr Leu His Thr Thr Ser Pro Thr Gln Arg His Leu Cys Gly Gly
385                 390                 395                 400

Ser Ile Ile Gly Asn Gln Trp Ile Leu Thr Ala Ala His Cys Phe Tyr
                405                 410                 415
```

Gly Val Glu Ser Pro Lys Ile Leu Arg Val Tyr Ser Gly Ile Leu Asn
            420                 425                 430

Gln Ser Glu Ile Lys Glu Asp Thr Ser Phe Phe Gly Val Gln Glu Ile
            435                 440                 445

Ile Ile His Asp Gln Tyr Lys Met Ala Glu Ser Gly Tyr Asp Ile Ala
            450                 455                 460

Leu Leu Lys Leu Glu Thr Thr Val Asn Tyr Thr Asp Ser Gln Arg Pro
465                 470                 475                 480

Ile Cys Leu Pro Ser Lys Gly Asp Arg Asn Val Ile Tyr Thr Asp Cys
            485                 490                 495

Trp Val Thr Gly Trp Gly Tyr Arg Lys Leu Arg Asp Lys Ile Gln Asn
            500                 505                 510

Thr Leu Gln Lys Ala Lys Ile Pro Leu Val Thr Asn Glu Glu Cys Gln
            515                 520                 525

Lys Arg Tyr Arg Gly His Lys Ile Thr His Lys Met Ile Cys Ala Gly
            530                 535                 540

Tyr Arg Glu Gly Gly Lys Asp Ala Cys Lys Gly Asp Ser Gly Gly Pro
545                 550                 555                 560

Leu Ser Cys Lys His Asn Glu Val Trp His Leu Val Gly Ile Thr Ser
            565                 570                 575

Trp Gly Glu Gly Cys Ala Gln Arg Glu Arg Pro Gly Val Tyr Thr Asn
            580                 585                 590

Val Val Glu Tyr Val Asp Trp Ile Leu Glu Lys Thr Gln Ala Val
            595                 600                 605

<210> SEQ ID NO 2
<211> LENGTH: 372
<212> TYPE: DNA
<213> ORGANISM: Mus musculus

<400> SEQUENCE: 2
caagttactc taaaagagtc tggccctggg atattgaagc cctcacagac cctcagtctg      60
acttgttctt tctctgggtt ttcactgagc acttctggta tgggtgtagg ctggattcgt     120
cagccttcag ggaagggtct ggagtggctg gcacacattt ggtgggatga tgataagtac     180
tataacccat ccctgaagag ccagctcaca atctccaagg atacctccag aaaccaggtt     240
ttcctcaaga tcaccagtgt ggacgctgca gatactgcca cttactactg tgctcgaaag     300
aggtcttcgg ttgtagccca ttactatgct atggactact ggggtcaagg aacctcagtc     360
accgtctcct ca                                                         372

<210> SEQ ID NO 3
<211> LENGTH: 124
<212> TYPE: PRT
<213> ORGANISM: Mus musculus

<400> SEQUENCE: 3

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
            35                  40                  45

Trp Leu Ala His Ile Trp Trp Asp Asp Asp Lys Tyr Tyr Asn Pro Ser
            50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Ala Ala Asp Thr Ala Thr Tyr Tyr
                85                  90                  95

Cys Ala Arg Lys Arg Ser Ser Val Val Ala His Tyr Tyr Ala Met Asp
            100                 105                 110

Tyr Trp Gly Gln Gly Thr Ser Val Thr Val Ser Ser
            115                 120

<210> SEQ ID NO 4
<211> LENGTH: 333
<212> TYPE: DNA
<213> ORGANISM: Mus musculus

<400> SEQUENCE: 4
gacattgtgc tgacccaatc tccagcttct ttggctgtgt ctctagggca gagggccacc      60
atctcctgca aggccagcca agtgttgat tatgatggtg atagttatct gaactggtac      120
caacagaaac aggacagcc acccaaactc ctcatctatg ctgcatccaa tctagaatct      180
gggatcccag ccaggtttag tggcagtggg tctgggacag acttcaccct caacatccat      240
cctgtggagg aggaggatgc tgcaacctat tactgtcagc aaagtaatgg ggatccgtgg      300
acgttcggtg gaggcaccaa gctggaaatc aaa                                  333

<210> SEQ ID NO 5
<211> LENGTH: 111
<212> TYPE: PRT
<213> ORGANISM: Mus musculus

<400> SEQUENCE: 5

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Gly Asp Pro Trp Thr Phe Gly Gly Gly Thr Lys Leu Glu Ile Lys
            100                 105                 110

<210> SEQ ID NO 6
<211> LENGTH: 372
<212> TYPE: DNA
<213> ORGANISM: Mus musculus

<400> SEQUENCE: 6
caagttactc taaaagagtc tggccctacc atagtgaagc ccacacagac cctcactctg      60
acttgttctt tctctgggtt ttcactgagc acttctggta tgggtgtagg ctggattcgt      120
cagccttcag ggaaggctct ggagtggctg gcacacattt ggtgggatga tgataagtac      180
tataacccat ccctgaagag ccggctcaca atcaccaagg atacctccaa aaaccaggtt      240
gtcctcacca tgaccaatat ggacgctgtg gatactgcca cttactactg tgctcgaaag      300

```
aggtcttcgg ttgtagccca ttactatgct atggactact ggggtcaagg aaccacagtc    360
accgtctcct ca                                                         372
```

<210> SEQ ID NO 7
<211> LENGTH: 124
<212> TYPE: PRT
<213> ORGANISM: Mus musculus

<400> SEQUENCE: 7

```
Gln Val Thr Leu Lys Glu Ser Gly Pro Thr Ile Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Gly Trp Ile Arg Gln Pro Ser Gly Lys Ala Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Lys Arg Ser Ser Val Val Ala His Tyr Tyr Ala Met Asp
            100                 105                 110

Tyr Trp Gly Gln Gly Thr Thr Val Thr Val Ser Ser
            115                 120
```

<210> SEQ ID NO 8
<211> LENGTH: 333
<212> TYPE: DNA
<213> ORGANISM: Mus musculus

<400> SEQUENCE: 8

```
gacattgtgc tgacccaatc tccagattct ttggctgtgt ctctagggga gagggccacc    60
atcacctgca aggccagcca agtgttgat tatgatggtg atagttatct gaactggtac    120
caacagaaac caggacagcc acccaaactc ctcatctatg ctgcatccaa tctagaatct    180
gggatcccag acaggtttag tggcagtggg tctgggacag acttcaccct caccatctct    240
tctgtgcagg aggaggatgt ggcaacctat tactgtcagc aaagtaatgg ggatccgtgg    300
acgttcggtg gaggcaccaa ggtggaaatc aaa                                  333
```

<210> SEQ ID NO 9
<211> LENGTH: 111
<212> TYPE: PRT
<213> ORGANISM: Mus musculus

<400> SEQUENCE: 9

```
Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80
```

```
Ser Leu Gln Glu Glu Asp Val Ala Thr Tyr Tyr Cys Gln Gln Ser Asn
            85                  90                  95

Gly Asp Pro Trp Thr Phe Gly Gly Gly Thr Lys Val Glu Ile Lys
           100                 105                 110

<210> SEQ ID NO 10
<211> LENGTH: 7
<212> TYPE: PRT
<213> ORGANISM: Mus musculus

<400> SEQUENCE: 10

Thr Ser Gly Met Gly Val Gly
1               5

<210> SEQ ID NO 11
<211> LENGTH: 16
<212> TYPE: PRT
<213> ORGANISM: Mus musculus

<400> SEQUENCE: 11

His Ile Trp Trp Asp Asp Asp Lys Tyr Tyr Asn Pro Ser Leu Lys Ser
1               5                   10                  15

<210> SEQ ID NO 12
<211> LENGTH: 14
<212> TYPE: PRT
<213> ORGANISM: Mus musculus

<400> SEQUENCE: 12

Lys Arg Ser Ser Val Val Ala His Tyr Tyr Ala Met Asp Tyr
1               5                   10

<210> SEQ ID NO 13
<211> LENGTH: 15
<212> TYPE: PRT
<213> ORGANISM: Mus musculus

<400> SEQUENCE: 13

Lys Ala Ser Gln Ser Val Asp Tyr Asp Gly Asp Ser Tyr Leu Asn
1               5                   10                  15

<210> SEQ ID NO 14
<211> LENGTH: 7
<212> TYPE: PRT
<213> ORGANISM: Mus musculus

<400> SEQUENCE: 14

Ala Ala Ser Asn Leu Glu Ser
1               5

<210> SEQ ID NO 15
<211> LENGTH: 9
<212> TYPE: PRT
<213> ORGANISM: Mus musculus

<400> SEQUENCE: 15

Gln Gln Ser Asn Gly Asp Pro Trp Thr
1               5
```

ANTI-FACTOR XI MONOCLONAL ANTIBODIES AND METHODS OF USE THEREOF

CROSS REFERENCE TO RELATED APPLICATIONS

This is a continuation of U.S. patent application Ser. No. 15/470,758, filed Mar. 27, 2017, which is a continuation of U.S. application Ser. No. 14/809,551, filed Jul. 27, 2015, now U.S. Pat. No. 9,636,399, issued May 2, 2017, which is a continuation of U.S. application Ser. No. 14/242,692, filed Apr. 1, 2014, now U.S. Pat. No. 9,125,895, issued Sep. 8, 2015, which is a continuation of U.S. application Ser. No. 13/783,952, filed Mar. 4, 2013, now abandoned, which is a divisional of U.S. application Ser. No. 13/446,320, filed Apr. 13, 2012, now U.S. Pat. No. 8,399,648, issued Mar. 19, 2013, which is a divisional of U.S. application Ser. No. 12/744,037, filed Oct. 13, 2010, now U.S. Pat. No. 8,236,316, issued Aug. 7, 2012, which is the U.S. National Stage of International Application No. PCT/US2008/084336, filed Nov. 21, 2008, published in English under PCT Article 21(2), which claims the benefit of U.S. Provisional Application No. 60/989,523, filed Nov. 21, 2007. All of the above-listed applications are herein incorporated by reference in their entirety.

FIELD OF THE INVENTION

The present invention relates to antibodies capable of binding to factor XI and methods of use thereof, particularly methods of use as antithrombotic agents that do not compromise hemostasis.

BACKGROUND OF THE INVENTION

Hemostasis is a vital function that stops bleeding and protects the integrity of blood circulation on both molecular and macroscopic levels. Hemostasis includes a coagulation cascade of sequentially activatable enzymes that is traditionally divided into three parts: 1) an intrinsic pathway, which includes interactions of blood coagulation proteins that lead to the generation of coagulation factor IXa without involvement of coagulation factor VIIa; 2) an extrinsic pathway, which includes interactions of blood coagulation proteins that lead to the generation of coagulation factor Xa and/or IXa without involvement of thromboplastin antecedent (factor XI); and 3) a common coagulation pathway, including interactions of blood coagulation proteins II, V, VIII, IX and X that lead to the generation of thrombin (factor IIa). Thrombin activates platelets and generates fibrin, both of which are essential building elements of the hemostatic plug that is responsible for sealing the vascular breach. Complete absence of thrombin or platelets causes paralysis of hemostasis and leads to lethal hemorrhage.

Thrombosis, like hemostasis, is a platelet and thrombin dependent process. Thrombosis is a pathological, intravascular, thrombin-dependent, progressive deposition of polymerized fibrin and activated platelets that causes occlusion of blood vessels in various organs. In healthy mammals, intravascular coagulation is localized to the site of hemostasis. Intraluminal progression into thrombosis is efficiently blocked by natural antithrombotic enzymes and inhibitors, such as activated protein C, plasmin, and antithrombin. Thrombosis develops when the antithrombotic system fails to control further intravascular thrombin generation. Causality of macrovascular and/or microvascular thrombosis in morbidity and mortality has been directly documented in various diseases that include deep vein thrombosis, pulmonary thromboembolism, peripheral artery thrombosis and embolism, retina vein thrombosis, as well as myocardial infarction (Meadows (1965) *Med. J. Aust.* 4:409-411; Harland (1966) *Lancet* 26:1158-1160), ischemic stroke (Carmon (1966) *J. Neural. Sci.* 4:111-119), anthrax sepsis and meningococcal sepsis (Dalldorf (1977) *Arch. Pathol. Lab. Med.* 101:6-9), or heparin-induced thrombocytopenia (Rhodes (1973) *Surg. Gynecol. Obstet.* 136:409-416). Evidence for organ damage of thrombotic occlusion and hypoxic origin is also available in other disease groups, such as hemorrhagic fevers (Dennis (1969) *Br. J. Haematol.* 17:455-462; Gear (1979) *Rev. Infect. Dis.* 1:571-591; Ignatiev (2000) *Immunol. Lett.* 71:131-140), diabetic angiopathy (Ishibashi (1981) *Diabetes* 30:601-606; Boeri (2001) *Diabetes* 50:1432-1439), kidney disease (Miller (1980) *Kidney Int.* 18:472-479; McCutcheon (1993) *Lupus* 2:99-103), and several other conditions.

Although thrombosis and hemostasis are not identical molecular processes, they are similar enough that antithrombotic drugs developed to date inadvertently target both. Thrombosis is treated with antiplatelet, profibrinolytic, and anticoagulant agents, yet most of these agents can completely block both thrombosis and hemostasis when administered at their maximally effective doses. Antithrombotic drugs either target the building blocks of thrombi (fibrin and platelets) or inhibit molecules (coagulation factors) and cells (platelets) from participating in the thrombus-forming process. It is widely believed among clinicians and researchers that if an antithrombotic agent is unable to block hemostasis it will not work in thrombosis.

One of the oldest anticoagulant antithrombotic agents, heparin, is still the most widely given injection in the world. Sufficiently high doses of heparin can achieve nearly 100% efficacy but only at the cost of paralyzing hemostasis at such doses. Unfortunately, newer antithrombotic agents, such as fractionated heparins or direct thrombin inhibitors agents do not fare much better. As a result, antithrombotic agents, especially anticoagulants and profibrinolytic agents, must be administered at less than their maximally efficacious doses, and thrombosis remains an under-treated disease. Introduction of new compounds that are based on the promise of improved efficacy but are unable to promise improvement of hemostatic safety is unjustifiable. To date, antithrombotic compounds have fallen short of promising improvement of safety. The ideal antithrombotic agent would anti-coagulate circulating blood without adversely affecting hemostasis.

Thus, there remains a pressing medical need for the development of safe yet efficacious agents that block intravascular thrombin generation without paralyzing hemostasis.

BRIEF SUMMARY OF THE INVENTION

Compositions and methods are provided for inhibiting thrombosis without compromising hemostasis. Compositions include anti-factor XI monoclonal antibodies (aX-IMabs) capable of binding to an epitope on the heavy chain of human FXI, particularly the A3 domain of the heavy chain of human FXI. Compositions also include epitope-binding fragments, variants, and derivatives of the monoclonal antibodies, cell lines producing these antibody compositions, and isolated nucleic acid molecules encoding the amino acid sequences of the antibodies. The invention further includes pharmaceutical compositions comprising the anti-factor XI monoclonal antibodies of the invention, or epitope-binding fragments, variants, or derivatives thereof, in a pharmaceutically acceptable carrier. Methods of the invention comprise administering the compositions described above to a subject in need thereof for the purpose of inhibiting thrombosis, reducing a required dose of an antithrombotic agent in the treatment of thrombosis, treating metastatic cancer, or treating an acute inflammatory reaction. Methods for making an anti-factor XI monoclonal antibody, or epitope-binding fragments, variants, or derivatives thereof, are also provided.

BRIEF DESCRIPTION OF THE DRAWINGS

(FIG. 1A) Qualitative schematic of the local sampling method (not to scale). (FIG. 1B) Scanning electron microscope image of uncoated, and collagen coated (FIG. 1C) expanded-polytetrafluoroethylene (ePTFE) clinical vascular graft material.

(FIGS. 4A, 4C) Local and (FIGS. 4C, 4D) systemic thrombin/antithrombin (TAT) and β-thromboglobulin (β-TG) levels during thrombus formation, respectively. Blood samples were also tested for the fibrinolysis product dimer (FIG. 4E). Local values are those taken from the near wall, low flow boundary layer 1 cm distal to the growing thrombus over the course of 10 min prior to its designated time, while systemic samples were taken from the arterio/venous shunt proximal to the thrombogenic device. Zero time points in all groups are from samples taken systemically immediately before each study. FXI inhibition dramatically reduced local thrombin formation and platelet activation, which translated into significant systemic reductions in both TAT and β-TG compared with collagen controls by 60 min. Significant fibrinolysis was not detected in either non-treated or aXIMab treated animals.

(FIG. 7A) Binding of anti-factor XI monoclonal antibody 1A6 to Factor XI using Western Blots. The bands in the left panel show that antibody 1A6 recognizes Factor XI in human and non-human primate plasma. Similar bands were not observed for Factor XI depleted or deficient samples (right panel). (FIG. 7B) aXIMab prevented visible fibrin formation and reduced platelet accumulation in FXII-inhibited or deficient human blood under flow.

(FIG. 8C) Western blot of 1 μl NHP and NBP samples size fractionated by non-reducing 7.5% SDS-PAGE. Detection was with a polyclonal antibody against human FXI. The five lanes on the right represent samples prior to (0) or 1, 6, 8, and 27 days after infusion of aXIMab. Abbreviations: XI—100 ng purified human FXI; NHP—normal human plasma; NBP—normal baboon plasma; XI-DP—FXI deficient human plasma.

FIG. 9 shows Western Blots of the binding of anti-factor XI monoclonal antibody 1A6 to chimeric proteins of FXI and Prekallikrein (PK) involving the substitution of FXI domains with PK domains. As shown in the right panel, monoclonal antibody 1A6 bound all FXI/PK chimeras except the chimera in which the A3 domain of FXI was substituted with a PK domain.

FIG. 12 shows the position of Alanine substitutions within the A3 domain of FXI that prevented or reduced the binding of monoclonal antibody 1A6 to FXI.

FIGS. 13A-13D. (FIG. 13A) Aximab heavy chain nucleotide (SEQ ID NO: 2) and amino acid (SEQ ID NO: 3) sequences. (FIG. 13B) Aximab light chain nucleotide (SEQ ID NO: 4) and amino acid (SEQ ID NO: 5) sequences. (FIG. 13C) CDR grafted Aximab heavy chain nucleotide (SEQ ID NO: 6) and amino acid (SEQ ID NO: 7) sequences. (FIG. 13D) CDR grafted Aximab light chain nucleotide (SEQ ID NO: 8) and amino acid (SEQ ID NO: 9) sequences. CDR definitions and protein sequence numbering according to Kabat. CDR nucleotide and protein sequences are in bold. Changes from murine sequence are underlined in (FIG. 13C) and (FIG. 13D). Human acceptor germline framework is IGHV2-5.

DETAILED DESCRIPTION

I. Overview

Figure 1A:
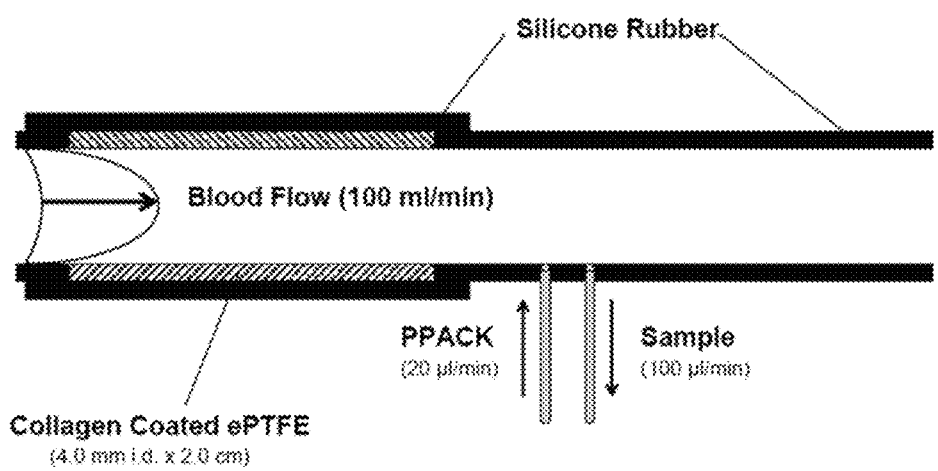
FIGS. 1A-1C. Local sampling model and thrombogenic device used to initiate thrombus formation.

The present invention relates to compositions and methods relating to anti-factor XI monoclonal antibodies (aXIMabs) for inhibiting thrombosis without compromising hemostasis. As described more fully below, monoclonal antibodies from a mouse cell line designated 1A6 were prepared that recognized and bound to the heavy chain of primate (particularly human) factor XI (FXI), particularly to the Apple 3 (A3) domain of the heavy chain of human FXI. Although polyclonal anti-FXI antibodies are commercially available for research and diagnostic uses, these polyclonal antibodies are not safe to use in the clinic because they cannot be controlled and their production is dependent on the availability of live animals (See, e.g., Gruber & Hanson (2003) *Blood* 102:953-955). In contrast, monoclonal antibodies can be consistently manufactured in cell cultures, they can be synthesized, or purified from byproducts of transgenic organisms that can range from fungi to plants to animals. In addition, although mouse monoclonal anti-FXI antibodies are currently available for research applications, no specific anti-factor XI monoclonal antibodies have been produced for use as safe antithrombotic agents in vivo.

One advantage of the anti-factor XI monoclonal antibodies of the invention, or epitope-binding fragments, variants, or derivatives thereof, is their exceptional safety as anticoagulant agents. The anti-factor XI monoclonal antibodies of the invention are monospecific for FXI and do not inhibit essential proteins or interact with vital molecules and pathways, either in their intact form or when degraded. This is a particular safety advantage as compared to other antithrombotic agents. Specifically, doses of anti-factor XI monoclonal antibody significantly exceeding the maximum effective dose (for example, several times the maximum effective dose) did not produce any adverse bleeding or other toxic side effects in subjects. In contrast, all other antithrombotic agents, such as vitamin K antagonists, indirect and direct inhibitors of essential coagulation enzymes, platelet inhibitors, fibrinolytic agents, and the like are ultimately dangerous and even fatal when they are administered at their maximally effective doses.

Other safety advantages of the anti-factor XI monoclonal antibodies of the invention as compared to other antithrombotic agents, such as small molecule enzyme inhibitors or platelet inhibitors, are that the monoclonal antibodies of the invention are metabolized and eliminated without generation of toxic metabolic intermediates, and their metabolism is virtually independent of the integrity of liver and kidney functions. In addition, the anti-factor XI monoclonal antibodies of the invention do not interact with other pharmacological compounds and do not directly affect the activity or metabolism of other drugs, in contrast to other antithrombotic agents.

The anti-factor XI monoclonal antibodies of the invention are also useful as potent pharmacological agents. As described more fully below, anti-factor XI monoclonal antibody administration can prevent or treat diseases where FXI activity contributes to pathology. The anti-factor XI monoclonal antibodies of the invention inhibit thrombus formation without causing bleeding and therefore provide a safe treatment option for thromboocclusive diseases in subjects, particularly humans. Another advantage of anti-factor XI monoclonal antibody as compared to other antithrombotic agents is that a single dose is safe and effective for longer than one week. Most antithrombotic agents have shorter duration of action.

II. Definitions

It is to be noted that the term "a" or "an" entity refers to one or more of that entity; for example, "an anti-factor XI monoclonal antibody" is understood to represent one or more anti-factor XI monoclonal antibodies. As such, the terms "a" (or "an"), "one or more," and "at least one" can be used interchangeably herein.

The term "hemostasis" as used herein refers to a coordinated mechanism that maintains the integrity of blood circulation following injury to the vascular system. In normal circulation without vascular injury, platelets are not activated and freely circulate. Vascular injury exposes subendothelial tissue to which platelets can adhere. Adherent platelets will attract other circulating platelets to form a preliminary plug that is particularly useful in closing a leak in a capillary or other small vessel. These events are termed primary hemostasis. This is, typically, rapidly followed by secondary hemostasis that involves a cascade of linked enzymatic reactions that result in plasma coagulation to reinforce the primary platelet plug. Accordingly, a hemostatic agent is any agent that slows or stops bleeding by promoting or enhancing any of the physiological processes involved in hemostasis, including contraction of the blood vessels, adhesion and aggregation of formed blood elements, and blood or plasma coagulation.

The term "coagulation" as used herein refers to the process of polymerization of fibrin monomers, resulting in the transformation of blood or plasma from a liquid to a gel phase. Coagulation of liquid blood may occur in vitro, intravascularly or at an exposed and injured tissue surface. In vitro blood coagulation results in a gelled blood that maintains the cellular and other blood components in essentially the same relative proportions as found in non-coagulated blood, except for a reduction in fibrinogen content and a corresponding increase in fibrin. By "blood clot" is intended a viscous gel formed of, and containing all, components of blood in the same relative proportions as found in liquid blood.

The term "coagulation cascade" as used herein refers to three interconnecting enzyme pathways as described, for example, by Manolin in Wilson et al. (eds): Harrison's Principle of Internal Medicine, 14th Ed. New York. McGraw-Mill, 1998, p. 341, incorporated herein by reference in its entirety. The intrinsic coagulation pathway leads to the formation of Factor IXa, that in conjunction with Factors VIIIa and X, phospholipid and $Ca^{2+}$ gives Factor Xa. The extrinsic pathway gives Factor Xa and IXa after the combination of tissue factor and factor VII. The common coagulation pathway interacts with the blood coagulation Factors V, VIII, IX and X to cleave prothrombin to thrombin (Factor IIa), which is then able to cleave fibrinogen to fibrin. As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-factor XI monoclonal antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-factor XI monoclonal antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Derivatives of anti-factor XI monoclonal antibodies and antibody polypeptides of the present invention, are polypeptides that have been altered so as to exhibit additional features not found on the reference antibody or antibody polypeptide of the invention. Examples include fusion proteins. Variant polypeptides may also be referred to herein as "polypeptide analogs." As used herein a "derivative" of an anti-factor XI monoclonal antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-factor XI monoclonal antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an anti-factor XI monoclonal antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription and translation control regions are well known in the art.

The present invention is directed to certain anti-factor XI monoclonal antibodies, or antigen-binding fragments, variants, or derivatives thereof. Unless specifically referring to full-sized antibodies such as naturally occurring antibodies, the term "anti-factor XI monoclonal antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) *Antibodies: A Laboratory Manual* (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM IgA, IgD, or IgE, respectively. The immunoglobulin subclasses (isotypes) e.g., $IgG_1$, $IgG_2$, $IgG_3$, $IgG_4$, $IgA_1$, etc., are well characterized and are known to confer functional specialization. Modified versions of each of these classes and isotypes are readily discernable to the skilled artisan in view of the instant disclosure and, accordingly, are within the scope of the instant invention. Although all immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000 Daltons. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology referred to as the "constant region" and the "variable region." The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$, or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art since they have been precisely defined (see, "Sequences of Proteins of Immunological Interest," Kabat et al. (1983) U.S. Department of Health and Human Services; and Chothia and Lesk (1987) *J. Mol. Biol.*, 196:901-917, which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk (1987) *J. Mol. Biol.* 196:901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. Those skilled in the art can routinely determine which residues comprise a particular CDR given the variable region amino acid sequence of the antibody.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-factor XI monoclonal antibody or antigen-binding fragment, variant, or derivative thereof of the present invention are according to the Kabat numbering system.

Antibodies or antigen-binding fragments, variants, or derivatives thereof of the invention include, but are not limited to monoclonal, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to anti-factor XI monoclonal antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains.

As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

Anti-factor XI monoclonal antibodies, or antigen-binding fragments, variants, or derivatives thereof disclosed herein may be described or specified in terms of the epitope(s) or portion(s) of an antigen, e.g., a target polypeptide (human factor XI, described in SEQ ID NO:1) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by anti-factor XI monoclonal antibodies of the present invention is located on the heavy chain of human factor XI and contains a sequence of at least 4, at least 5, at least 6, at least 7, more preferably at least 8, at least 9, at least 10, at least 15, at least 20, at least 25, or between about 15 to about 30 contiguous or non-contiguous amino acids of human factor XI (SEQ ID NO:1).

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$, or $10^{-3}$ sec$^{-1}$. More preferably, an antibody of the invention may be said to bind a target polypeptide disclosed herein or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$, or $10^{-7}$ sec$^{-1}$.

An antibody or antigen-binding fragment, variant, or derivative thereof disclosed herein may be said to bind a target polypeptide disclosed herein or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$, or $5\times10^4$ M$^{-1}$ sec$^{-1}$. More preferably, an antibody of the invention may be said to bind a target polypeptide disclosed herein or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, $5\times10^6$ M$^{-1}$ sec$^{-1}$, or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) *Antibodies: A Laboratory Manual* (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-factor XI monoclonal antibodies or antigen-binding fragments, variants or derivatives thereof of the invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the human factor XI antigen. A human framework region that has been engineered in this manner would thus comprise a mixture of human and donor framework residues, and is referred to herein as a "partially human framework region." Given the explanations set forth in, e.g., U.S. Pat. Nos. 5,585,089, 5,693,761, 5,693,762, and 6,180,370 it will be well within the competence of those skilled in the art, either by carrying out routine experimentation or by trial and error testing to obtain a functional engineered or humanized antibody.

For example, humanization of an anti-factor XI monoclonal antibody can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human anti-factor XI monoclonal antibody. See also U.S. Pat. Nos. 5,225,539; 5,585,089; 5,693,761; 5,693,762; 5,859,205; herein incorporated by reference. The resulting humanized anti-factor XI monoclonal antibody would comprise at least one rodent or mutant rodent CDR within the fully human framework regions of the variable domain of the heavy and/or light chain of the humanized antibody. In some instances, residues within the framework regions of one or more variable domains of the humanized anti-factor XI monoclonal antibody are replaced by corresponding non-human (for example, rodent) residues (see, for example, U.S. Pat. Nos. 5,585,089; 5,693,761; 5,693,762; and 6,180,370), in which case the resulting humanized anti-factor XI monoclonal antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein the term "properly folded polypeptide" includes polypeptides (e.g., anti-factor XI monoclonal antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g., by recombinant techniques, in vitro peptide synthesis, by enzymatic or chemical coupling of peptides or some combination of these techniques).

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of a disease state. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, non-human primates, domestic animals, farm animals, and zoo, sports, or pet animals such as dogs, cats, guinea pigs, rabbits, rats, mice, horses, cattle, cows, and the like.

As used herein, phrases such as "a subject that would benefit from administration of an anti-factor XI monoclonal antibody" and "an animal in need of treatment" includes subjects, such as mammalian subjects, that would benefit from administration of an anti-factor XI monoclonal antibody used, e.g., for inhibiting thrombosis with an anti-factor XI monoclonal antibody.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) *Molecular Cloning A Laboratory Manual* (2nd ed.; Cold Spring Harbor Laboratory Press); Sambrook et al., ed. (1992) *Molecular Cloning: A Laboratory Manual*, (Cold Springs Harbor Laboratory, NY); D. N. Glover ed., (1985) *DNA Cloning*, Volumes I and II; Gait, ed. (1984) *Oligonucleotide Synthesis*; Mullis et al. U.S. Pat. No. 4,683,195; Hames and Higgins, eds. (1984) *Nucleic Acid Hybridization*; Hames and Higgins, eds. (1984) *Transcription And Translation*; Freshney (1987) *Culture Of Animal Cells* (Alan R. Liss, Inc.); *Immobilized Cells And Enzymes* (IRL Press) (1986); Perbal (1984) *A Practical Guide To Molecular Cloning*; the treatise, *Methods In Enzymology* (Academic Press, Inc., N.Y.); Miller and Calos eds. (1987) *Gene Transfer Vectors For Mammalian Cells*, (Cold Spring Harbor Laboratory); Wu et al., eds., *Methods In Enzymology*, Vols.

154 and 155; Mayer and Walker, eds. (1987) *Immunochemical Methods In Cell And Molecular Biology* (Academic Press, London); Weir and Blackwell, eds., (1986) *Handbook Of Experimental Immunology*, Volumes I-IV; *Manipulating the Mouse Embryo*, Cold Spring Harbor Laboratory Press, Cold Spring Harbor, N.Y., (1986); and in Ausubel et al. (1989) *Current Protocols in Molecular Biology* (John Wiley and Sons, Baltimore, Md.).

General principles of antibody engineering are set forth in Borrebaeck, ed. (1995) *Antibody Engineering* (2nd ed.; Oxford Univ. Press). General principles of protein engineering are set forth in Rickwood et al., eds. (1995) *Protein Engineering, A Practical Approach* (IRL Press at Oxford Univ. Press, Oxford, Eng.). General principles of antibodies and antibody-hapten binding are set forth in: Nisonoff (1984) *Molecular Immunology* (2nd ed.; Sinauer Associates, Sunderland, Mass.); and Steward (1984) *Antibodies, Their Structure and Function* (Chapman and Hall, New York, N.Y.). Additionally, standard methods in immunology known in the art and not specifically described are generally followed as in *Current Protocols in Immunology*, John Wiley & Sons, New York; Stites et al., eds. (1994) *Basic and Clinical Immunology* (8th ed; Appleton & Lange, Norwalk, Conn.) and Mishell and Shiigi (eds) (1980) *Selected Methods in Cellular Immunology* (W.H. Freeman and Co., NY).

Standard reference works setting forth general principles of immunology include *Current Protocols in Immunology*, John Wiley & Sons, New York; Klein (1982) *J. Immunology: The Science of Self-Nonself Discrimination* (John Wiley & Sons, NY); Kennett et al., eds. (1980) *Monoclonal Antibodies, Hybridoma: A New Dimension in Biological Analyses* (Plenum Press, NY); Campbell (1984) "Monoclonal Antibody Technology" in *Laboratory Techniques in Biochemistry and Molecular Biology*, ed. Burden et al., (Elsevere, Amsterdam); Goldsby et al., eds. (2000) *Kuby Immunnology* (4th ed.; H. Freemand & Co.); Roitt et al. (2001) *Immunology* (6th ed.; London: Mosby); Abbas et al. (2005) *Cellular and Molecular Immunology* (5th ed.; Elsevier Health Sciences Division); Kontermann and Dubel (2001) *Antibody Engineering* (Springer Verlan); Sambrook and Russell (2001) *Molecular Cloning: A Laboratory Manual* (Cold Spring Harbor Press); Lewin (2003) *Genes VIII* (Prentice Hall 2003); Harlow and Lane (1988) *Antibodies: A Laboratory Manual* (Cold Spring Harbor Press); Dieffenbach and Dveksler (2003) *PCR Primer* (Cold Spring Harbor Press).

III. Human Factor XI

Human Factor XI is a two-chain glycoprotein with a molecular weight of approximately 160,000 daltons. The two chains are identical disulfide bonded polypeptides with molecular weights of approximately 80,000 daltons. Factor XI is activated to factor XIa by Factor XIIa. The amino acid sequence of human factor XI has been determined (see, e.g., Fujikawa et al. (1986) *Biochemistry* 25:2417-2424) and is provided as SEQ ID NO:1. In humans, the gene for FXI is located at the distal end of chromosome 4 (4q35.2) and contains 15 exons spread over ~25 kb of genomic DNA (Asaki et al. (1987) *Biochemistry* 26:7221-7228; Kato et al. (1989) *Cytogenet. Cell Genet.* 52:77).

The cleavage site for the activation of factor XI by factor XIIa is an internal peptide bond between Arg-369 and Ile-370 in each polypeptide chain (Fujikawa et al. (1986) *Biochemistry* 25:2417-2424). Each heavy chain of factor XIa (369 amino acids) contains four tandem repeats of 90-91 amino acids called apple domains (designated A1-A4) plus a short connecting peptide (Fujikawa et al. (1986) *Biochemistry* 25:2417-2424; Sun et al. (1999) *J. Biol. Chem.* 274: 36373-36378). The light chains of factor XIa (each 238 amino acids) contain the catalytic portion of the enzyme with sequences that are typical of the trypsin family of serine proteases (Fujikawa et al. (1986) *Biochemistry* 25:2417-2424). XIa proteolytically cleaves its substrate, factor IX, in an interaction requiring the factor XI A3 domain (Sun, Y., and Gailani, D. (1996) *J. Biol. Chem.* 271, 29023-29028).

IV. Anti-Factor XI Monoclonal Antibodies

In one embodiment, the present invention is directed to anti-factor XI monoclonal antibodies, including antigen-binding fragments, variants, or derivatives thereof. As used herein, the term "anti-factor XI monoclonal antibody" is an antibody that specifically recognizes human factor XI, particularly an epitope in the A3 domain of the heavy chain of human FXI (positions 182 to 265 of SEQ ID NO:1). In one embodiment, the epitope comprises 1, 2, 3, 4, 5, 6, 7, 8, 9, 10, 11, 12, 13, 14, 15, or more amino acids of the A3 domain of human FXI. In another embodiment, the epitope is selected from the group consisting of: a) amino acids 183 to 197 of SEQ ID NO:1; b) amino acids 203 to 204 of SEQ ID NO:1; c) amino acids 234 to 236 of SEQ NO:1; d) amino acids 241 to 243 of SEQ ID NO:1; e) amino acids 252 to 254 of SEQ ID NO:1; and f) amino acids 258 to 260 of SEQ ID NO:1. In particular embodiments, the epitope is selected from the group consisting of: a) amino acids 183 to 197 of SEQ ID NO:1; b) amino acids 252 to 254 of SEQ ID NO:1; and c) amino acids 258 to 260 of SEQ ID NO:1.

In another embodiment, the anti-factor XI monoclonal antibodies of the invention have binding specificity to an antigen that is a peptide comprising 2 or more amino acids out of the A3 domain of the heavy chain of human FXI (positions 182 to 265 of SEQ ID NO:1). In yet another embodiment, the anti-factor XI monoclonal antibodies of the invention have binding specificity to an antigen that is a peptide comprising an amino acid sequence selected from the group consisting of: a) amino acids 183 to 197 of SEQ ID NO:1; b) amino acids 203 to 204 of SEQ ID NO:1; c) amino acids 234 to 236 of SEQ ID NO:1; d) amino acids 241 to 243 of SEQ ID NO:1; e) amino acids 252 to 254 of SEQ ID NO:1; and f) amino acids 258 to 260 of SEQ ID NO:1. In particular embodiments, the anti-factor XI monoclonal antibodies of the invention have binding specificity to an antigen that is a peptide comprising an amino acid sequence selected from the group consisting of: a) amino acids 183 to 197 of SEQ ID NO:1; b) amino acids 252 to 254 of SEQ ID NO:1; and c) amino acids 258 to 260 of SEQ ID NO:1.

The anti-factor XI monoclonal antibodies of the invention, including antigen-binding fragments, variants, or derivatives thereof, are biologically active. The term "biologically active" as used herein refers to one or more of the following physiological activities associated with the anti-thrombotic activity of the anti-factor XI monoclonal antibodies of the invention: 1) inhibition of the coagulation activity of activated factor XI; 2) prevention of the activation of factor XI; and 3) acceleration of the clearance of factor XI from the circulatory system of a subject.

In one embodiment, the term "biologically active" refers to inhibiting the coagulation activity of activated human factor XI. The phrase "inhibit the coagulation activity" as used herein refers to decreasing the ability of activated factor XI to produce blood clot formation. Methods for determining whether the coagulation activity has been inhibited include the use of assays for measuring clot strength and/or the length of time before clot formation in plasma or whole blood samples. Accordingly, inhibiting coagulation activity as used herein refers to at least partially reversing the effect of an coagulant, including at least 5% reversal, at least 10% reversal, at least 20% reversal, at least 30% reversal, at least 40% reversal, at least 50% reversal, at least 60% reversal, at least 70% reversal, at least 80% reversal, at least 90% reversal, and up to and including 100% reversal. The term "reversal" as used herein refers to a lengthening of the time to onset of clot formation or a decrease in clot strength. Assays for measuring the onset of clot formation and clot strength are well known in the art and include activated partial thromboplastin time (APTT), thromboelastography (TEG®), and continuous monitoring of thrombin generation using the Thrombinoscope® system (see, for example, Banez et al. (1980) *Am. J. Clin. Pathol.*, 74:569-574; van den Besselaar et al. (1990) *Thromb. Haemost.*, 63:16-23; Kawasaki et al. (2004) *Anesthesia & Analgesia*, 99:1440-1444; Hemker et al. (2003) *Pathophysiology of Haemostasis & Thrombosis*, 33:4-15).

In one embodiment, the monoclonal antibody of the invention is produced by hybridoma cell line 1A6.

The present invention also relates to humanized anti-factor XI antibodies that bind to human factor XI. In some embodiments, the anti-factor XI antibodies of the invention comprise at least one optimized complementarity-determining region (CDR). By "optimized CDR" is intended that the CDR has been modified and optimized sequences selected based on the sustained or improved binding affinity and/or anti-factor XI activity that is imparted to an anti-factor XI antibody comprising the optimized CDR. "Anti-factor XI activity" or "factor XI blocking activity" can include one or more of the following physiological activities, as described elsewhere herein: 1) inhibition of the coagulation activity of activated factor XI; 2) prevention of the activation of factor XI; and 3) acceleration of the clearance of factor XI from the circulatory system of a subject.

The modifications involve replacement of amino acid residues within the CDR such that an anti-factor XI antibody retains specificity for the factor XI antigen and has improved binding affinity and/or improved anti-factor XI activity. Anti-factor XI activity of an anti-factor XI antibody of the invention is improved as compared to aXIMab (1A6) in a functional assay as described herein. The novel anti-factor XI antibodies of the invention and suitable antigen-binding fragments, variants, and derivatives thereof also exhibit anti-factor XI activity that is at least similar to that exhibited by aXIMab (1A6), as measured in standard assays. The optimized CDRs of the invention are utilized in $V_H$ and $V_L$ domains of the heavy and light chains, respectively, of anti-factor XI antibodies. Exemplary anti-factor XI antibodies of the invention comprise a $V_H$ domain selected from the group consisting of SEQ ID NO:3 and 7, and/or a $V_L$ domain selected from the group consisting of SEQ ID NO:5 and 9.

The anti-factor XI antibodies of the invention comprise at least one optimized complementarity-determining region (CDR). By "optimized CDR" is intended that the CDR has been modified and optimized sequences selected based on the improved binding affinity and/or improved CDC activity that is imparted to an anti-factor XI antibody comprising the optimized CDR. The modifications involve replacement of amino acid residues within the CDR such that an anti-factor XI antibody retains specificity for the factor XI antigen and has improved or sustained binding affinity and/or anti-factor XI activity. Anti-factor XI activity of an anti-factor XI antibody of the invention is improved or sustained as compared to aXIMab (1A6) in a functional assay as described herein. The optimized CDRs of the invention are utilized in $V_H$ and $V_L$ domains of the heavy and light chains, respectively, of anti-human factor XI antibodies. Exemplary anti-factor XI antibodies of the invention comprise a $V_H$ domain selected from the group consisting of SEQ ID NO:3 and 7, and/or a $V_L$ domain selected from the group consisting of SEQ ID NO:5 and 9.

In some embodiments, the anti-factor XI antibodies of the invention comprise optimized CDRs. That is, the anti-factor XI antibodies of the invention comprise at least one optimized CDR amino acid sequence selected from the group consisting of SEQ ID NO:10-15 or amino acid sequences having at least about 65%, about 70%, about 75%, about 80%, about 85%, about 90%, about 95%, about 96%, about 97%, about 98%, about 99%, or 100% sequence identity to a sequence selected from the group consisting of SEQ ID NO:10-15. That is, the optimized CDRs comprise the sequences set forth in SEQ ID NO:10-15 and the sequences of SEQ ID NO:10-15 having at least one, two, three, four, or five amino acid substitutions, depending upon the CDR involved.

Thus, in some embodiments, the anti-factor XI antibodies of the invention comprise a $V_H$ domain having at least one optimized CDR selected from the group consisting of:
  a) a CDR comprising the amino acid sequence set forth in SEQ ID NO:10, 11, or 12; and
  b) a CDR comprising an amino acid sequence having at least 85% sequence identity to the amino acid sequence set forth in SEQ ID NO:10, 11, or 12.

In other embodiments, the anti-factor XI antibodies of the invention comprise a $V_L$ domain having at least one optimized CDR selected from the group consisting of:
  a) a CDR comprising the amino acid sequence set forth in SEQ ID NO:13, 14, or 15; and
  b) a CDR comprising an amino acid sequence having at least 85% sequence identity to the amino acid sequence set forth in SEQ ID NO:13, 14, or 15.

In other embodiments, the anti-factor XI antibodies of the invention comprise a $V_H$ domain and a $V_L$ domain, wherein said $V_H$ domain has at least one optimized CDR comprising the amino acid sequence set forth in SEQ ID NO:10, 11, or 12, and wherein said $V_L$ domain has at least one optimized CDR comprising the amino acid sequence set forth in SEQ ID NO:13, 14, or 15.

In some embodiments, the anti-factor XI antibodies comprising at least one of the optimized CDRs of the invention are IgG kappa immunoglobulins. In such embodiments, the IgG kappa immunoglobulin can comprise a human IgG1, IgG2, IgG3, or IgG4 constant region within a heavy chain of the immunoglobulin and a human kappa constant region within a light chain of the immunoglobulin. In particular embodiments, the IgG kappa immunoglobulin comprises fully or partially human framework regions within the variable domain of the heavy chain and within the variable domain of the light chain. In other embodiments, the IgG kappa immunoglobulin comprises murine framework regions within the variable domain of the heavy chain and within the variable domain of the light chain.

In further embodiments of the invention, the anti-factor XI antibodies of the invention comprise a $V_H$ domain having an amino acid sequence set forth in SEQ ID NO:3 or 7 and/or a $V_L$ domain having an amino acid sequence set forth in SEQ ID NO:5 and 9, or amino acid sequences having at least about 80%, 85%, about 90%, about 91%, about 92%, about 93%, about 94%, about 95%, about 96%, about 97%, about 98%, about 99% or 100% sequence identity to a sequence set forth in SEQ ID NO:3, 5, 7, and 9.

In yet other embodiments of the invention, the anti-factor XI antibodies of the invention comprise a $V_H$ domain, where the $V_H$ domain is selected from the group consisting of:

a) a $V_H$ domain comprising an amino acid sequence set forth in SEQ ID NO:3 or 7; and b) a $V_H$ domain comprising an amino acid sequence having at least 85% sequence identity to an amino acid sequence set forth in SEQ ID NO:3 or 7.

In another embodiment of the invention, the anti-factor XI antibodies of the invention comprise a $V_L$ domain, where the $V_L$ domain is selected from the group consisting of:

a) a $V_L$ domain comprising an amino acid sequence set forth in SEQ ID NO:5 or 9; and b) a $V_L$ domain comprising an amino acid sequence having at least 85% sequence identity to an amino acid sequence set forth in SEQ ID NO:5 or 9.

Methods for measuring anti-factor XI antibody binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al. (2000) *Immunity* 13:633-642; Kumanogoh et al. (2002) *J Immunol* 169:1175-1181; Watanabe et al. (2001) *J Immunol* 167:4321-4328; Wang et al. (2001) *Blood* 97:3498-3504; and Giraudon et al. (2004) *J Immunol* 172(2):1246-1255, all of which are herein incorporated by reference.

Suitable biologically active variants of the anti-factor XI antibodies can be used in the methods of the present invention. Such variants will retain the desired binding properties of the parent anti-factor XI antibody. Methods for making antibody variants are generally available in the art. For example, amino acid sequence variants of an anti-factor XI antibody, an antibody region, or an antibody variable domain of a heavy or light chain, can be prepared by mutations in the cloned DNA sequence encoding the amino acid sequence of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, New York); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found, Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly⇔Ala, Val⇔Ile, Leu⇔Asp, Glu⇔Lys, Arg⇔Asn, Gln⇔Phe, and Phe⇔Trp⇔Tyr.

In constructing variants of the anti-factor XI antibody polypeptides of interest, modifications are made such that variants continue to possess the desired properties, i.e., being capable of specifically binding to a human factor XI antigen expressed on the surface of or secreted by a human cell, and having factor XI blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an anti-factor XI antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference anti-factor XI antibody have amino acid sequences that have at least about 80%, about 85%, about 88%, about 90%, about 91%, about 92%, about 93%, about 94%, or about 95% sequence identity to the amino acid sequence for the reference anti-factor XI antibody molecule or to a shorter portion of the reference antibody molecule. More preferably, the molecules share at least about 96%, about 97%, about 98%, or about 99% sequence identity. When discussed herein, whether any particular polypeptide, including the constant regions, CDRs, $V_H$ domains, and $V_L$ domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Adv. Appl. Math.* 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference anti-factor XI antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

When any two polypeptide sequences are optimally aligned for comparison, it is recognized that residues appearing opposite of one another within the alignment occupy positions within their respective polypeptides that correspond to one another. Such positions are referred to herein as "corresponding positions" and the residues residing at corresponding positions are referred to as "corresponding residues" or residues that "correspond" to one another. Thus, for example, where a polypeptide of interest is optimally aligned to a reference polypeptide sequence having, for example, 10 residues, the residue within the polypeptide of interest appearing opposite residue 5 of the reference sequence is referred to as the "residue at the position corresponding to residue 5" of the reference sequence.

The precise chemical structure of a polypeptide capable of specifically binding factor XI and retaining the desired factor XI blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-factor XI antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-factor XI antibody used herein so long as the desired properties of the anti-factor XI antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (i.e., binding specificity for factor XI and factor XI blocking activity) do not remove the polypeptide sequence from the definition of anti-factor XI antibodies of interest as used herein.

The art provides substantial guidance regarding the preparation and use of polypeptide variants. In preparing the anti-factor XI antibody variants, one of skill in the art can readily determine which modifications to the native protein nucleotide or amino acid sequence will result in a variant that is suitable for use as a therapeutically active component of a pharmaceutical composition used in the methods of the present invention.

In certain anti-factor XI antibodies, the Fc portion may be mutated to decrease effector function using techniques known in the art. For example, the deletion or inactivation (through point mutations or other means) of a constant region domain may reduce FC receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

Anti-factor XI antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-factor XI polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a factor XI polypeptide) can be determined using techniques described herein or by routinely modifying techniques known in the art.

V. Fusion Proteins and Antibody Conjugates

Anti-factor XI monoclonal antibodies of the invention, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-factor XI monoclonal antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The present invention also provides for fusion proteins comprising an anti-factor XI antibody, or antigen-binding fragment, variant, or derivative thereof, and a heterologous polypeptide. For example, the heterologous polypeptide to which the antibody is fused may be useful for function, may increase the in vivo half life of the polypeptides, or may be a marker sequence that facilitates purification or detection (see, e.g., Leong et al. (2001) *Cytokine* 16:106; *Adv. in Drug Deliv. Rev.* (2002) 54:531; Weir et al. (2002) *Biochem. Soc. Transactions* 30:512; Gentz et al. (1989) *Proc. Natl. Acad. Sci. USA* 86:821-824; Wilson et al. (1984) *Cell* 37:767)

Fusion proteins can be prepared using methods that are well known in the art (see for example U.S. Pat. Nos. 5,116,964 and 5,225,538). The precise site at which the fusion is made may be selected empirically to optimize the binding characteristics of the fusion protein. DNA encoding the fusion protein is then transfected into a host cell for expression.

Anti-factor XI monoclonal antibodies of the present invention, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of a subject. In particular, Anti-factor XI monoclonal antibodies of the invention, or antigen-binding fragments, variants, or derivatives thereof, may be conjugated to therapeutic agents, prodrugs, peptides, proteins, enzymes, viruses, lipids, biological response modifiers, pharmaceutical agents, or PEG. Techniques for conjugating various moieties to an anti-factor XI antibody, or antigen-binding fragment, variant, or derivative thereof, are well known, see, e.g., Arnon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-56; Hellstrom et al. (1987) "Antibodies for Drug Delivery," in *Controlled Drug Delivery*, ed. Robinson et al. (2nd ed.; Marcel Dekker, Inc.), pp. 623-53); Thorpe (1985) "Antibody Carriers of Cytotoxic Agents in Cancer Therapy: A Review," in *Monoclonal Antibodies '84: Biological and Clinical Applications*, ed. Pinchera et al., pp. 475-506; "Analysis, Results, and Future Prospective of the Therapeutic Use of Radiolabeled Antibody in Cancer Therapy," in *Monoclonal Antibodies for Cancer Detection and Therapy*, ed. Baldwin et al., Academic Press, pp. 303-16 (1985); and Thorpe et al. (1982) "The Preparation and Cytotoxic Properties of Antibody-Toxin Conjugates," *Immunol. Rev.* 62:119-58.

VI. Polynucleotides Encoding Anti-Factor XI Antibodies

The present invention also provides for nucleic acid molecules encoding anti-factor XI antibodies of the invention, or antigen-binding fragments, variants, or derivatives thereof.

In one embodiment, the present invention provides an isolated polynucleotide comprising, consisting essentially of, or consisting of a nucleic acid encoding an immunoglobulin heavy chain domain ($V_H$ domain), where at least one of the CDRs of the $V_H$ domain has an amino acid sequence that is at least about 80%, about 85%, about 90%, about 95%, about 96%, about 97%, about 98%, about 99%, or identical to any one of SEQ ID NOS:10-12.

In another embodiment, the present invention provides an isolated polynucleotide comprising, consisting essentially of, or consisting of a nucleic acid encoding an immunoglobulin light chain domain ($V_L$ domain), where at least one of the CDRs of the $V_L$ domain has an amino acid sequence that is at least about 80%, about 85%, about 90%, about 95%, about 96%, about 97%, about 98%, about 99%, or identical to any one of SEQ ID NOS:13-15.

In a further embodiment, the present invention includes an isolated polynucleotide comprising, consisting essentially of, or consisting of a nucleic acid encoding a $V_H$ domain that has an amino acid sequence that is at least about 80%, about 85%, about 90%, about 91%, about 92%, about 93%, about 94%, about 95%, about 96%, about 97%, about 98%, about 99%, or 100% identical to a reference $V_H$ domain polypeptide sequence selected from the group consisting of SEQ ID NO:3 and 7, wherein an anti-factor XI antibody comprising the encoded $V_H$ domain specifically or preferentially binds to factor XI.

In a further embodiment, the present invention includes an isolated polynucleotide comprising, consisting essentially of, or consisting of a nucleic acid encoding a $V_L$ domain that has an amino acid sequence that is at least about 80%, about 85%, about 90%, about 91%, about 92%, about 93%, about 94%, about 95%, about 96%, about 97%, about 98%, about 99%, or 100% identical to a reference $V_L$ domain polypeptide sequence selected from the group consisting of SEQ ID NO:5 and 9, wherein an anti-factor XI antibody comprising the encoded $V_L$ domain specifically or preferentially binds to factor XI.

In another embodiment, the present invention provides an isolated polynucleotide comprising, consisting essentially of, or consisting of a nucleic acid that is at least about 80%, about 85%, about 90%, about 91%, about 92%, about 93%, about 94%, about 95%, about 96%, about 97%, about 98%, about 99%, or 100% identical to a reference polynucleotide sequence selected from the group consisting of SEQ ID NOS:2, 4, 6, and 8.

Any of the polynucleotides described above may further include additional nucleic acids, encoding, e.g., a signal peptide to direct secretion of the encoded polypeptide, antibody constant regions as described herein, or other heterologous polypeptides as described herein. Also, as described in more detail elsewhere herein, the present invention includes compositions comprising one or more of the polynucleotides described above. In one embodiment, the invention includes compositions comprising a first polynucleotide and second polynucleotide wherein said first polynucleotide encodes a $V_H$ domain as described herein and wherein said second polynucleotide encodes a $V_L$ domain as described herein. Specifically a composition which comprises, consists essentially of, or consists of a $V_H$ domain selected from the group consisting of SEQ ID NO:3 and 7, and/or a $V_L$ domain selected from the group consisting of SEQ ID NO:5 and 9.

The present invention also includes fragments of the polynucleotides of the invention, as described elsewhere. Additionally polynucleotides that encode fusion polypolypeptides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al. (1994) *BioTechniques* 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-factor XI antibody, or antigen-binding fragment, variant, or derivative thereof, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated front, or nucleic acid, preferably poly A+RNA, isolated front, any tissue or cells expressing the antibody or other anti-factor XI antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-factor XI antibody. Amplified nucleic acids generated by PCR may then be cloned into replicable cloning vectors using any method well known in the art.

Once the nucleotide sequence and corresponding amino acid sequence of the anti-factor XI antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) *Molecular Cloning, A Laboratory Manual* (2nd ed.; Cold Spring Harbor Laboratory, Cold Spring Harbor, N.Y.) and Ausubel et al., eds. (1998) *Current Protocols in Molecular Biology* (John Wiley & Sons, NY), which are both incorporated by reference herein in their entireties), to generate antibodies having a different amino acid sequence, for example to create amino acid substitutions, deletions, and/or insertions.

A polynucleotide encoding an anti-factor XI antibody, or antigen-binding fragment, variant, or derivative thereof, can be composed of any polyribonucleotide or polydeoxribonucleotide, which may be unmodified RNA or DNA or modified RNA or DNA. For example, a polynucleotide encoding anti-factor XI antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-factor XI antibody, or antigen-binding fragment, variant, or derivative thereof can be composed of triple-stranded regions comprising RNA or DNA or both RNA and DNA. A polynucleotide encoding an anti-factor XI antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

VII. Expression of Antibody Polypeptides

DNA sequences that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide anti-factor XI antibodies, or antigen-binding fragments, variants, or derivatives thereof, of the invention, the polynucleotides encoding the anti-factor XI antibodies are typically inserted in an expression vector for introduction into host cells that may be used to produce the desired quantity of anti-factor XI antibody.

Recombinant expression of an antibody, or fragment, derivative or analog thereof, e.g., a heavy or light chain of an antibody that binds to a target molecule described herein, e.g., factor XI, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthesized as discussed above. Of course, any expression vector that is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-factor XI antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in *Vectors*, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al. (1986) *Gene* 45:101; Cockett et al. (1990) *Bio/Technology* 8:2).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al. (1977) *Cell* 11:223), hypoxanthine-guanine phosphoribosyltransferase (Szybalska and Szybalski (1992) *Proc. Natl. Acad. Sci. USA* 48:202), and adenine phosphoribosyltransferase (Lowy et al. (1980) *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al. (1980) *Natl. Acad. Sci. USA* 77:357; O'Hare et al. (1981) *Proc. Natl. Acad. Sci. USA* 78:1527); gpt, which confers resistance to mycophenolic acid (Mulligan and Berg (1981) *Proc. Natl. Acad. Sci. USA* 78:2072); neo, which confers resistance to the aminoglycoside G-418 *Clinical Pharmacy* 12:488-505; Wu and Wu (1991) *Biotherapy* 3:87-95; Tolstoshev (1993) *Ann. Rev. Pharmacol. Toxicol.* 32:573-596; Mulligan (1993) *Science* 260:926-932; and Morgan and Anderson (1993) *Ann. Rev. Biochem.* 62:191-217 (1993); *TIB TECH* 11(5):155-215 (May, 1993); and hygro, which confers resistance to hygromycin (Santerre et al. (1984) *Gene* 30:147. Methods commonly known in the art of recombinant DNA technology which can be used are described in Ausubel et al. (1993) *Current Protocols in Molecular Biology* (John Wiley & Sons, NY); Kriegler (1990) "Gene Transfer and Expression" in *A Laboratory Manual* (Stockton Press, NY); Dracopoli et al. (eds) (1994) *Current Protocols in Human Genetics* (John Wiley & Sons, NY) Chapters 12 and 13; Colberre-Garapin et al. (1981) *J. Mol. Biol.* 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al. (1983) *Mol. Cell. Biol.* 3:257).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-factor XI antibodies, or antigen-binding fragments, variants, or derivatives thereof of the invention can also be expressed in non-mammalian cells such as bacteria or yeast or plant cells. Bacteria that readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al. (1983) *EMBO J.* 2:1791), in which the antibody coding sequence may be ligated individually into the vector in frame with the lacZ coding region so that a fusion protein is produced; pIN vectors (Inouye and Inouye (1985) *Nucleic Acids Res.* 13:3101-3109; Van Heeke and Schuster (1989) *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al. (1979) *Nature* 282:39; Kingsman et al. (1979) *Gene* 7:141; Tschemper et al. (1980) *Gene* 10:157) is commonly used. This plasmid already contains the TRP1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. Patent Application Publication No. 2002 0123057 A1.

VIII. Methods of Use for Anti-Factor XI Monoclonal Antibodies

Methods of the invention are directed to the use of anti-factor XI monoclonal antibodies, including antigen-binding fragments, variants, and derivatives thereof, to inhibit thrombosis in a subject in need thereof. Though the following discussion refers to methods and treatment of various diseases and disorders with anti-factor XI monoclonal antibody of the invention, the methods described herein are also applicable to the antigen-binding fragments, variants, and derivatives of these anti-factor XI monoclonal antibodies that retain the desired properties of the anti-factor XI monoclonal antibodies of the invention, i.e., capable of specifically binding human factor XI and being able to inhibit the coagulation activity of human factor XI.

Anti-factor XI monoclonal antibodies of the invention may be administered to any subject in which inhibition of thrombosis would be beneficial. In particular, it is contemplated that the anti-factor XI monoclonal antibodies of the invention are particularly useful as antithrombotic agents that do not compromise hemostasis, and as such are superior alternatives to traditional antithrombotic agents.

In one embodiment, the anti-factor XI monoclonal antibodies of the invention may be used to treat conditions characterized by vascular occlusions, such as those that occur as a result of thrombus formation. Conditions that are characterized by vascular occlusions and justify treatment or prevention using anti-factor XI monoclonal antibodies of the include those that involve the arterial, capillary, and venous vasculature.

In the coronary arteries, occlusive thrombus formation often follows the rupture of atherosclerotic plaque. This occlusion is the major cause of acute myocardial infarction and unstable angina. Coronary occlusions can also occur following infections, inflammation, thrombolytic therapy, angioplasty, and graft placements. Similar principles apply to other parts of the arterialvasculature and include, among others, thrombus formation in the carotid arteries, which is the major cause of transient or permanent cerebral ischemia and stroke.

Venous thrombosis often follows stasis, infections, inflammatory reactions, and major surgery of the lower extremities or the abdominal area. Deep vein thrombosis results in reduced blood flow from the area distal to the thrombus and predisposes to pulmonary embolism. Pulmonary embolism is a major cause of post-surgical mortality. Disseminated intravascular coagulation (DIC) and acute respiratory distress syndrome (ARDS) where the monoclonal antibodies of this invention are useful commonly occur within all vascular systems during bacterial sepsis, entry of foreign material into the blood stream following, e.g., trauma and child birth, immune reactions, inflammation, certain viral infections, certain platelet disorders, and cancer. Disseminated intravascular coagulation is a severe complication of many disease conditions and some drug treatments, including, for example, hepatin. Thrombotic consumption of coagulation factors and platelets, and systemic coagulation results in the formation of life-threatening thrombi occurring throughout the microvasculature leading to local or widespread hypoxia and organ failure.

Thus, in one embodiment, a method is provided for inhibiting thrombosis in a subject in need thereof comprising administering to the subject an effective dose of an anti-factor XI monoclonal antibody of the invention, particularly where the thrombosis is associated with: 1) acute coronary syndromes such as myocardial infarction, unstable angina, refractory angina, occlusive coronary thrombus occurring post-thrombolytic therapy or post-coronary angioplasty; 2) ischemic cerebrovascular syndromes including embolic stroke, thrombotic stroke, or transient ischemic attacks; 3) thrombosis occurring in the venous system occurring either spontaneously or in the setting of malignancy, trauma, or surgery, including pulmonary thromboembolism; 4) any coagulopathy including ARDS and DIC, e.g., in the setting of sepsis or other infection, surgery, pregnancy, trauma, or malignancy and whether associated with multi-organ failure or not, thrombotic thrombocytopenic purpura, thromboangiitis obliterans, or thrombotic disease associated with heparin induced thrombocytopenia; 5) thrombotic complications associated with extracorporeal circulation (e.g., renal dialysis, cardiopulmonary bypass or other oxygenation procedure, and plasmaphoresis); 6) thrombotic complications associated with instrumentation (e.g. cardiac or other intravascular catheterization, intraaortic balloon pump, and coronary stent or cardiac valve); and 7) complications associated with fitting of prosthetic devices.

As described elsewhere herein, traditional antithrombotic agents are dangerous or even fatal when administered at their maximally effective doses. Accordingly, in another embodiment, a method is provided for reducing a required dose or complementing the effect of an antithrombotic agent in the treatment of thrombosis in a subject in need thereof comprising administering to the subject an effective dose of an anti-factor XI monoclonal antibody of the invention.

Traditional antithrombotic agents include direct or indirect thrombin inhibitor, a Factor X inhibitor, a Factor IX inhibitor, a Factor XII inhibitor, a Factor V inhibitor, a Factor VIII inhibitor, a Factor XIII inhibitor, a Factor VII inhibitor, a tissue factor inhibitor, a profibrinolytic agent, a fibrinolytic or fibrinogenolytic agent, a carboxypeptidase B inhibitor, a platelet inhibitor, a selective platelet count reducing agent, or a Factor XI inhibitor.

Direct thrombin inhibitors include argatroban and derivatives or analogs thereof, hirudin and recombinant or synthetic derivatives or analogs thereof, derivatives of the tripeptide Phe-Pro-Arg, chloromethylketone derivatives, ximelagatran and derivatives, metabolites, or analogs thereof, anion binding exosite inhibitors, and RNA/DNA aptamers.

Indirect thrombin inhibitors include heparin, coumarin, dermatan, and thrombomodulin.

Factor X inhibitors include direct factor Xa inhibitors, rivaroxaban, antibodies to factor X, inactivated factor Xa, or analogs and derivatives thereof.

Factor IX inhibitors include antibodies to factor IX, direct factor IXa inhibitors, or inactivated factor IXa, or analogs and derivatives thereof.

Factor XII inhibitors include direct factor XII inhibitors, corn trypsin inhibitor, antibodies to FXII, or inactivated factor XIIa or analogs and derivatives thereof.

Factor V inhibitors include antibodies to factor V, activated protein C, protein S, or analogs and derivatives thereof.

Factor VIII inhibitors include antibodies to FVIII, activated protein C, protein S, or analogs and derivatives thereof.

Factor XIII inhibitors include antibodies to factor XIII, direct factor XIIIa inhibitors, or inactivated factor XIIIa.

Factor VII inhibitors include antibodies to factor VII, tissue factor pathway inhibitor, inactivated factor VIIa, or direct factor VIIa inhibitor or analogs and derivatives thereof.

Tissue factor inhibitors include tissue factor pathway inhibitor, antibodies to tissue factor, or analogs and derivatives thereof.

Profibrinolytic agents include urokinase, streptokinase, tissue plasminogen activator or derivatives thereof.

Fibrinolytic or fibrinogenolytic agents include plasmin, microplasmin, ancrod, or derivatives thereof.

Platelet inhibitors include aspirin, clopidogrel, dypiridamol, or derivatives thereof.

Selective platelet count reducing agents include hydroxyurea, anagrelide, or derivatives thereof.

Factor XI inhibitors include direct factor XIa inhibitors, other antibodies to factor XI, inactivated factor XIa, or analogs and derivatives thereof.

In another embodiment, a method is provided for treating metastatic cancer in a subject in need thereof comprising administering to the subject an effective dose of an anti-factor XI monoclonal antibody of the invention.

In yet another embodiment, a method is provided for treating an acute inflammatory reaction in a subject in need thereof comprising administering to the subject an effective dose of an anti-factor XI monoclonal antibody of the invention.

In further embodiments of the present invention, combination therapies are provided in which an anti-factor XI monoclonal antibody is the primary active agent and is administered along with an additional active agent to a subject in need thereof. Such combination therapy may be carried out by administration of the different active agents in a single composition, by concurrent administration of the different active agents in different compositions, or by sequential administration of the different active agents. The combination therapy may also include situations where the anti-factor XI monoclonal antibody is already being administered to the patient, and the additional active agent is to be added to the patient's drug regimen, as well as where different individuals (e.g., physicians or other medical professionals) are administering the separate components of the combination to the patient.

The additional active agent will generally, although not necessarily, be one that is effective in inhibiting thrombosis. In a preferred embodiment, the additional active agent is a hemostatic agent, i.e., an agent that promotes hemostasis. Particularly preferred hemostatic agents for use in the combination therapies of the present invention include activated factor VII (FVIIa) or activated prothrombin complex concentrate (APCC). Both FVIIa and APCC were developed as hemostatic agents for the treatment of bleeding in patients with inhibitor-developing hemophilia (Scharrer (1999) *Haemophilia*, 5:253-259; Shapiro et al. (1998) *Thromb. Haemost.*, 80:773-778; Lusher et al. (1980) *N. Engl. J. Med.*, 303:421-425; Sjamsoedin et al. (1981) *N. Engl. J. Med.*, 305:717-21; Negrier et al. (1997) *Thromb. Haemost.*, 77:1113-1119). The key active ingredient of APCC is prothrombin, which contributes to both hemostasis and thrombus growth (Akhavan et al. (2000) *Thromb. Haemost.*, 84:989-997; Xi et al. (1989) *Thromb. Haemost.*, 62:788-791). By contrast, increasing the plasma concentration of FVIIa is thought to increase the generation of thrombin predominantly through a tissue factor (TF) dependent pathway in which the TF/FVIIa complex activates factors IX and X (Hoffman and Monroe (2001) *Thromb. Haemost.*, 85:958-965).

IX. Pharmaceutical Compositions and Administration Methods

The anti-factor XI monoclonal antibodies of the invention, or antigen-binding fragments, variants, or derivatives thereof, can be formulated according to known methods for preparing pharmaceutically useful compositions, such as by admixture with a pharmaceutically acceptable carrier vehicle. Suitable vehicles and their formulations are described, for example, in *Remington's Pharmaceutical Sciences* (16th ed., Osol, A. (ed.), Mack, Easton Pa. (1980)). In order to form a pharmaceutically acceptable composition suitable for effective administration, such compositions will contain an effective amount of the anti-factor XI monoclonal antibody, or antigen-binding fragments, variants, or derivatives thereof, either alone, or with a suitable amount of carrier vehicle.

The term "pharmaceutically acceptable" as used herein refers to a therapeutic agent or compound that while biologically active will not damage the physiology of the recipient human or animal to the extent that the viability of the recipient is comprised.

Pharmaceutical compositions may be administered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired.

Pharmaceutical compositions may be formulated for immediate release or controlled release. The "absorption pool" represents a solution of the drug administered at a particular absorption site, and $k_r$, $k_a$, and $k_e$ are first-order rate constants for: 1) release of the drug from the formulation; 2) absorption; and 3) elimination, respectively. For immediate release dosage forms, the rate constant for drug release $k_r$ is far greater than the absorption rate constant $k_a$. For controlled release formulations, the opposite is true, i.e., $k_r <<< k_a$, such that the rate of release of drug from the dosage form is the rate-limiting step in the delivery of the drug to the target area. The term "controlled release" as used herein includes any nonimmediate release formulation, including but not limited to sustained release, delayed release and pulsatile release formulations.

Pharmaceutical compositions comprising anti-factor XI monoclonal antibodies of the invention, or antigen-binding fragments, variants, or derivatives thereof, can be administered in dosages and by techniques well known to those skilled in the medical or veterinary arts, taking into consideration such factors as the age, sex, weight, species and condition of the particular subject, and the route of administration. The route of administration can be via any route that delivers a safe and therapeutically effective dose of an anti-factor XI monoclonal antibody of the invention, or antigen-binding fragments, variants, or derivatives thereof, to the blood of an animal or human. Forms of administration, include, but are not limited to, systemic, topical, enteral, and parenteral routes of administration. Enteral routes include oral and gastrointestinal administration. Parenteral routes include intravenous, intraarterial, intramuscular, intraperitoneal, subcutaneous, transdermal, and transmucosal administration. Other routes of administration include epidural or intrathecal administration.

The effective dosage and route of administration are determined by the therapeutic range and nature of the compound, and by known factors, such as the age, weight, and condition of the subject, as well as $LD_{50}$ and other screening procedures that are known and do not require undue experimentation.

The term "dosage" as used herein refers to the amount of an anti-factor XI monoclonal antibody of the invention, or antigen-binding fragments, variants, or derivatives thereof, administered to an animal or human. The therapeutic agent may be delivered to the recipient as a bolus or by a sustained (continuous or intermittent) delivery. When the delivery of a dosage is sustained over a period, which may be in the order of a few minutes to several days, weeks or months, or may be administer chronically for a period of years, the dosage may be expressed as weight of the therapeutic agent/kg body weight of the patient/unit time of delivery.

By "therapeutically effective dose or amount" or "effective amount" is intended an amount of an anti-factor XI monoclonal antibody that when administered brings about a positive therapeutic response with respect to treatment of a patient in need thereof. In some embodiments of the invention, a therapeutically effective dose of the anti-factor XI monoclonal antibody is in the range from about 0.01 mg/kg to about 10 mg/kg, from about 0.1 mg/kg to about 10 mg/kg, from about 1 mg/kg to about 10 mg/kg, from about 1 mg/kg to about 5 mg/kg, from about 0.01 mg/kg to about 1 mg/kg, or from about 0.1 mg/kg to about 1 mg/kg. In other embodiments, the therapeutically effective doses of anti-factor XI monoclonal antibody, is about 0.01 mg/kg, about 0.03 mg/kg, about 0.1 mg/kg, about 0.3 mg/kg, about 0.5 mg/kg, about 1 mg/kg, about 1.5 mg/kg, about 2 mg/kg, about 2.5 mg/kg, about 3 mg/kg, about 5 mg/kg, about 7 mg/kg, about 10 mg/kg, or other such doses falling within the range of about 0.01 mg/kg to about 10 mg/kg. It is recognized that the method of treatment may comprise a single administration of a therapeutically effective dose or multiple administrations of a therapeutically effective dose of the anti-factor XI monoclonal antibody.

The following examples are offered by way of illustration and not by way of limitation.

EXPERIMENTAL

Example 1. Inhibition of Factor XI with Monoclonal Antibody 1A6 Decreases Thrombin Production and Prevents Vascular Occlusion in Experimental Thrombosis in Primates The present study in primates was designed to help clarify the role of FXI in thrombus formation, and to determine if FXI inhibition represents a relatively safe thrombosis specific approach for limiting thrombus propagation. By measuring local procoagulant and fibrinolytic markers, uniquely sensitive time dependent measurements of local thrombin production, platelet activation, and fibrinolysis were assessed. In order to delineate the role of FXI, studies were also performed using a potent monospecific antibody to FXI. Platelet and fibrin deposition on thrombogenic devices were assessed, and vascular graft occlusion studies were performed to determine the importance of FXI in the propagation and stability of relatively large experimental thrombi under arterial type shear. These results demonstrate for the first time in vivo that FXI is capable of facilitating robust thrombin generation and platelet activation on the flow surface of forming thrombi, which contributes directly to thrombus growth and stability. These results also show that FXI related inhibition of fibrinolysis plays, at most, a minor role in limiting the degradation of rapidly propagating arterial type thrombi.

Methods

Experimental Animals.

A total of 39 non-terminal studies were performed on 17 normal juvenile male baboons (*Papio anubis*) weighing 9-11 kg. Experiments were conducted on non-anticoagulated awake animals that had chronic exteriorized arterio-venous (AV) shunts previously placed between the femoral artery and vein, as described elsewhere (Hanson et al. (1993) *J. Clin. Invest.* 92:2003-2012). Baseline shunt blood flow exceeded 250 ml/min in all study animals. Anxiety was managed with low dose ketamine (<2 mg/kg/hr). Platelet counts, red cell counts, and hematocrits were measured daily, before and after the experiments. Calculated blood loss did not exceed 4% of total blood volume on any experimental day.

Thrombosis Model.

Figure 1B:
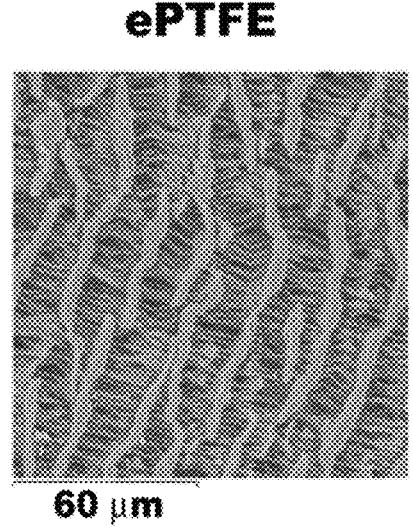
Figure 1C:
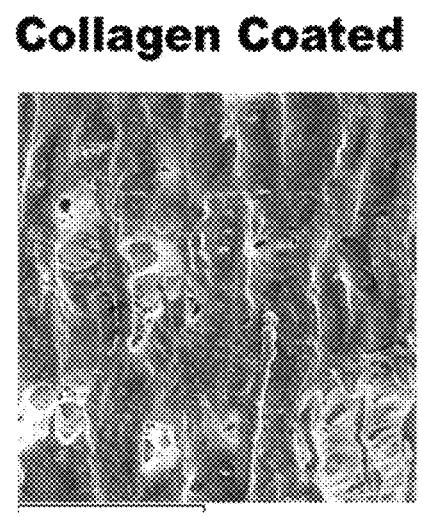

Thrombus formation was initiated within the baboon AV shunt by interposing a thrombogenic segment of prosthetic vascular graft (ePTFE, WL Gore & Co., Flagstaff, Ariz.), as previously described (Hanson et al. (1993) *J. Clin. Invest.* 92:2003-2012). To consistently trigger platelet-dependent thrombus formation, the clinical graft segments were coated with immobilized collagen. Twenty mm long grafts having internal diameters (i.d.) of either 2 or 4 mm were filled with equine type I collagen (1 mg/ml; Nycomed Arzenmittel, Munich, Germany) for 15 min, and then dried overnight under sterile airflow. This method produced a uniform collagen coating within the graft lumen as determined by scanning electron microscopy (FIGS. 1B and 1C). The thrombogenic collagen-coated grafts were then incorporated between segments of silicon rubber tubing, and deployed into the AV shunts (FIG. 1A). The grafts were exposed to blood for up to 60 min. During each experiment, the blood flow rate through the graft was restricted to 100 ml/min by clamping the proximal silicone rubber shunt segment, thereby producing a mean wall shear rate (MWSR) in the 4 mm grafts of 265 s$^{-1}$, while in the 2 mm grafts the initial MWSR was 2120 s$^{-1}$. Flow rates were continuously monitored using an ultrasonic flow meter (Transonics Systems, Ithaca, N.Y.). The 4 mm grafts did not occlude and pulsatile flow rates remained at 100 ml/min until the thrombogenic graft segments were removed at 60 min. Baseline blood flow was restored through the permanent shunt after each experiment. In the 2 mm diameter grafts blood flow rates progressively declined due to thrombus formation. The grafts were removed from the AV shunts when the flow rate fell from 100 ml/min to below 20 ml/min, signaling imminent occlusion. The time from initiation of blood flow to graft removal (<20 ml/min blood flow) was taken as the occlusion time.

For imaging of the platelet deposition, autologous baboon platelets were labeled with 1 mCi of $^{111}$In-oxine as previously described (Hanson et al. (1993) *J. Clin. Invest.* 92:2003-2012). Labeled platelets were infused and allowed to circulate for at least 1 h before studies were performed. Accumulation of labeled platelets onto thrombogenic grafts were measured in 5-min intervals using a gamma scintillation camera. Homologous $^{125}$I-labeled baboon fibrinogen (4 µCi, >90% clottable) was infused 10 min before each study, and incorporation of the labeled fibrin within the thrombus was assessed using a gamma counter 30 days later to allow the $^{111}$In to decay. The radioactivity deposited (cpm) was divided by the clottable fibrin(ogen) radioactivity of samples taken at the time of the original study (cpm/mg).

Occlusion studies were performed using 10 mm long 2 mm i.d. collagen coated devices which produced high arterial shear rates (2120 s$^{-1}$ at 100 ml/min clamped blood flow). Accumulation of labeled platelets onto 2 mm thrombogenic grafts were measured in 3-min intervals using a gamma scintillation camera. Flow was maintained at 100 ml/min by proximal clamping for as long as possible, and then allowed to decrease as the propagating thrombus began to occlude the device. A final blood flow rate of 20 ml/min was used as a cutoff for occlusion, since a fully occlusive thrombi and lack of blood flow through the device could lead to occlusion of the shunt and a significant loss of blood for the animals.

Sampling Method.

A novel local sampling method was used to assess the local production of thrombogenic mediators by sampling blood that superfused propagating experimental thrombi. Since thrombotic markers can be rapidly degraded and cleared from circulation, systemic sampling may lack the sensitivity to detect more subtle changes, and does not establish the location of such marker generation. All blood samples were collected into ⅒$^{th}$ volume 3.8% citrate anticoagulant. Systemic samples (1 ml each) were collected before initiation of thrombosis as well as 30 and 60 min into each study. A total of 6 local blood samples were drawn from the peripheral blood IBL at a rate of 100 µl/min over 10 min intervals out of a 0.64 mm port which was located 10 mm distal to the growing thrombus (FIG. 1A). In order to maintain patency of the sample port, Phe-Pro-Arg-chloromethylketone (PPACK, 0.5 mg/ml) anticoagulant, which directly inhibits thrombin, FVIIa, FXa, FXIa, and various other serine proteases (Angliker et al. (1988) *Biochem J.* 256:481-486), was infused immediately upstream at a rate of 20 µl/min, also using a 0.64 mm port. Infusion and sampling were regulated by syringe pumps (Harvard Apparatus). Local sampling was performed only with the 4 mm i.d. devices in this study. PPACK did not affect systemic prothrombin times (PT) or activated partial thromboplastin times (aPTT) that were measured in sequential plasma samples, nor did local sampling with PPACK affect platelet or fibrin deposition onto collagen-coated grafts as compared with historical results in this model.

For control studies, normal length silicone rubber extension tubing was used without inserting a thrombogenic device. The tubing was cut and reattached in the same location of graft insertion. Sample and anticoagulant infusion ports were positioned as described above, and blood samples were collected using the same approach. This provided a control of the local sampling technique to determine if this method produced activation of platelets and the coagulation pathway independent of the thrombogenic device. Consistent with previous studies (Savage et al. (1986) *Blood* 68:386-393), the silicone tubing was not measurably thrombogenic; neither the silicone polymer nor the sampling technique employed produced significant coagulation pathway or platelet activation.

Blood Sample Analysis.

Blood cell counts were determined using a micro-60 automated cell counter (Horiba-ABX Diagnostics). Blood samples were divided into two aliquots and processed according to specific test requirements. All samples were placed on ice for 10 min, centrifuged at 4° C. for 10 min at 12,900 g, and the plasmas were stored at −80° C. For β-thromboglobulin (βTG) determinations, the samples were supplemented with 4 µg/ml prostaglandin E1 (PGE$_1$), 4.3 mg/ml acetylsalicylic acid (ASA), and 50 µg/ml PPACK. Cross-reacting ELISA assays were used to determine D-dimer levels (IMUCLONE® D-Dimer, American Diagnostica; LOD: 35 ng/mL), the platelet activation marker βTG (Asserachrom®, Diagnostica Stago; LOD: 5 IU/mL), and thrombin-antithrombin complexes (TAT, Enzygnost-TAT, Dade-Behring; LOD: 2 ng/mL). All ELISA test kits utilized for these studies have previously shown sensitivity to baboon markers.

Factor XI and Platelet Inhibition In Vivo.

Since previous studies showed that polyclonal antibodies to human FXI required very high doses to achieve inhibition of FXI in baboons (Gruber et al. (2003) *Blood* 102:953-955), a new reagent was generated: a potent neutralizing anti-human FXI monoclonal antibody (aXIMab) that cross-reacted with baboon FXI. Hybridomas were derived from Balb/c mice immunized with purified human FXI using standard procedures (de StGroth & Scheidegger (1980) *J. Immunol. Methods* 35:1-21). Hybridomas were screened using solid phase ELISA against human FXI, and those that showed binding were subcloned twice by limiting dilution. The clone that produced the most potent neutralizing antibody, which inhibited both the activation of FXI and the activity of FXIa, was selected based on prolongation of the clotting time of recalcified normal human plasma (NHP) and normal baboon plasma (NBP) by the cell culture supernatant. The cell line producing aXIMab (1A6) was grown in a CL1000 bioreactor according to the manufacturer's protocol (Integra Biosciences), and the antibody was purified from the media using cation exchange and protein A chromatography.

Figure 7B:
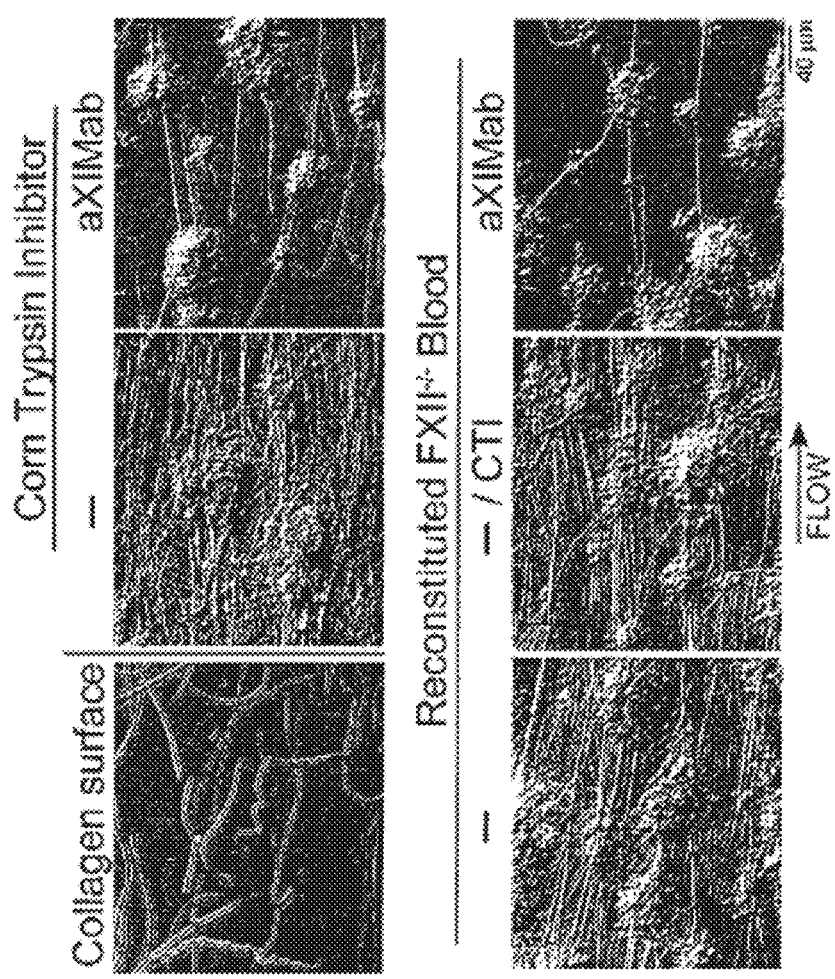
FIGS. 7A-7B.
Figure 7A:
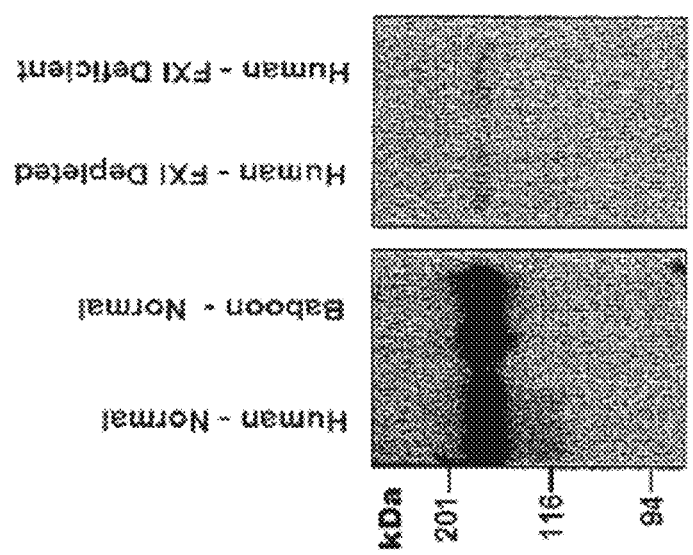

Human and baboon FXI in plasma was recognized by aXIMab as a single band at 160 kDa on Western blots (FIG. 7A). The antibody specifically recognized the third apple (A3) domain of the FXI heavy chain, as assessed by immunoblotting of recombinant FXI/prekallikrein chimeras (see Example 2 below; see also Sun et al. (1996) *J. Biol. Chem.* 271:29,023-29,028). The IC$_{50}$ and IC$_{99}$ of aXIMab in vitro was 2.5 nM and 10 nM, respectively, in a clotting assay using FXI deficient human plasma (George King Bio-Medical) with serial dilutions of NBP as standards (Proctor et al. (1961) *Am. J. Clin. Pathol.* 36:212-219). Purified aXIMab (monoclonal antibody 1A6), tested within a concentration range from 0-40 nM, prolonged the activated partial thromboplastin time (aPTT) (Hemosil™ SynthASil, Instrumentation Laboratory) similarly in both NHP and NBP in a concentration-dependent manner without affecting the prothrombin time (PT) (Innovin®, Dade Behring).

Pharmacological Inhibition of FXI and Platelet Activities In Vivo.

In a pilot experiment, aXIMab (monoclonal antibody 1A6; 2 mg/kg) was administered to a single baboon, and blood samples were collected into citrate anticoagulant over 4 weeks to measure circulating FXI antigen (FXI:Ag) concentrations, FXI inhibitor, and FXI procoagulant activity of each sample. This dose of aXIMab was chosen with the intent to achieve sustained and near-complete inhibition of FXI, assuming an initial dilution of the antibody into 60 ml blood volume per kg body weight after injection. The maximum achievable prolongation of the aPTT was about 2.5 fold. FXI:Ag was measured by ELISA using goat anti-human FXI polyclonal capture and detection (horseradish peroxidase conjugated [HRP]) antibodies (Affinity Biologicals, Hamilton, Ontario), which also recognized baboon FXI and its complex with aXIMab. A standard curve was constructed with serial dilutions of NBP, and FXI concentrations were determined in percentage of NBP. Western blots for FXI were performed by size fractionation of 1 µl samples of plasma under non-reducing conditions on 7.5% polyacrylamide-SDS gels, followed by transfer to PVDF membranes. Detection was with a goat-anti-human FXI polyclonal antibody conjugated to HRP and chemiluminescence. In the same samples, the Bethesda assay (Kasper et al. (1975) *Thromb. Diath. Haemorrh.* 34:869-872) was used to determine excess (non-complexed) circulating FXI inhibitor (aXIMab) activity levels, and the FXI procoagulant activity was assayed using a clotting assay (Proctor et al. (1961) *Am. J. Clin. Pathol.* 36:212-219).

aXIMab was administered as a single bolus (2 mg/kg intravenously) at least 24 h before the thrombosis experiments. The anticoagulant effect (aPTT) was monitored daily, and thrombosis experiments were performed while the FXI procoagulant activity in the circulating blood was reduced by ≥99%, as assessed by comparing the clotting times to a standard curve generated with FXI deficient human plasma (George King Bio-Medical). The PT was also assessed in all baboons and no differences were seen between groups.

We previously showed that inhibition of FXI by polyclonal antibodies is safer and as effective as high dose heparin in baboons (Gruber & Hanson (2003) *Blood* 102: 953-955). Since aspirin is a less antihemostatic agent than heparin, and it is often included in the standard treatment of arterial-type platelet-dependent thrombosis, ASA was used in the current studies with the occlusion-prone 2 mm i.d. grafts as a long-acting positive control. ASA (32 mg/kg) was administered orally 2-4 h before each thrombosis experiment, as described previously (Hanson et al. (1985) *J. Clin. Invest.* 75:1591-1599). Four weeks were allowed for washout of each aXIMab and ASA before performing new experiments in the same animal.

Hemostatic Assessment.

The effects of FXI inhibition and aspirin on primary hemostasis in baboons were assessed using the standard template skin bleeding time test (Surgicutt®, International Technidyne Corp). Experimentally, this and similar tests (e.g., Simplate bleeding times) have been shown to be sensitive to the effects of therapeutic anticoagulants, antiplatelet agents, and coagulation abnormalities in humans and non-human primates (Gruber et al. (2007) *Blood* 109: 3733-3740; Smith et al. (1985) *Am. J. Clin. Pathol.* 83:211-215; Payne et al. (2002) *J. Vasc. Surg.* 35:1204-1209). All bleeding time measurements were performed by the same expert technician. For indirect assessment of hemostasis, aPTT and PT measurements were also performed.

Computational Modeling.

A 3D computational fluid dynamics model, similar to that presented by Xu et al. ((2004) *Biorheology* 41:113-125), was used to estimate the concentrations of thrombus-derived macromolecules in blood that flows over forming thrombus and transports the markers along the adjacent vessel wall distally. The model was based on the geometry shown in FIG. 1A, with typical values for blood density and viscosity (Fung (1993) "Biomechanics: Mechanical Properties of Living Tissues" (ed 2nd). New York: Springer-Verlag). The model of local blood sampling was implemented using the finite element software ADINA (Watertown, Mass.). In addition, a 2D axisymmetric computational model, similar to that of Markou et al. ((1998) *Annals Biomed. Engineering* 26:502-511), was used to estimate thrombosis marker distribution within the flow field. Computational modeling predicted that molecules of interest (βTG, fibrin D-dimer, and TAT) released or generated at sites of thrombus formation, would be concentrated (>99%) within a very thin peripheral blood boundary layer (~0.1 mm thick concentration boundary layer) along the immediately distal vessel wall (data not shown). Thus, as employed here, the local sampling method effectively sampled the entire near-wall boundary layer region, immediately distal to the forming thrombus, for platelet and coagulation markers of interest.

Flow Chamber Coagulation Studies.

Glass capillary tubes were coated with 100 µg/ml Horm collagen (Nycomed Arzenmittel, Munich, Germany). Whole human blood was collected into corn trypsin inhibitor (CTI, 40 µg/ml), discarding the first 1 ml to limit any activation of the coagulation pathway, and then perfused through the tubes at a shear rate of 265 $s^{-1}$ for 10 min. Prior to each experiment, blood was incubated with aXIMab (20 µg/ml), or PBS vehicle. In separate experiments, washed platelets and RBCs were processed as described (McCarty et al. (2006) *J. Thromb. Haemost.* 4:1367-1378), and then mixed with FXII deficient human plasma (<1% FXII, Haematologic Technologies, Essex Junction, Vt.) to reach a hematocrit of 40% and platelet count of $300 \times 10^3$/µl. The reconstituted blood was incubated with aXIMab (20 µg/ml) or CTI (40 µg/ml), recalcified with 7.5 mM $CaCl_2$ and 3.75 mM $MgCl_2$, and then perfused immediately through collagen coated capillary tubes. Recalcified FXII deficient human plasma without RBCs or platelets was also perfused over collagen. Images were obtained by DIC microscopy after three minutes of perfusion with modified Tyrodes buffer.

Data Analysis.

Mean values are given ±1 SEM (standard error of the mean). Occlusion data were compared using the log-rank test. The two-tailed Student's t-test was used for all other single pair comparisons. A P value ≤0.05 was considered significant.

Results

Inhibition of FXI by aXIMab In Vitro Prevents Fibrin Formation Independent of FXIIa.

When whole human blood, which was anticoagulated with CTI to block the function of FXIIa, was perfused over collagen at arterial shear (265 $s^{-1}$), platelets were deposited in large aggregates which became enveloped by forming fibrin strands (FIG. 7B). In stark contrast, when CTI blood was treated with aXIMab to inhibit FXI, fibrin deposition was noticeably attenuated with a modest reduction in platelet adhesion. The outcome was similar when using reconstituted FXII deficient blood, with or without CTI. Again, fibrin was generated independent of FXII, and FXI inhibition with aXIMab interrupted fibrin formation. No fibrin was formed when recalcified FXII deficient human plasma was perfused over collagen. For these experiments, human whole blood, anticoagulated with CTI (40 µg/ml) to inhibit FXIIa, or reconstituted FXII deficient human blood was perfused through collagen coated capillary tubes at a shear rate of 265 s$^{-1}$ for 10 minutes. Prior to each experiment, blood was incubated with either aXIMab (20 µg/ml), CTI (40 µg/ml) for reconstituted blood where indicated, or PBS vehicle. Images were obtained via Kohler-illuminated Nomarski differential interference contrast (DIC) microscopy with a Zeiss Axiovert 200M microscope using a Zeiss 63× oil immersion 1.40 NA plan-apochromat lens. Images were captured following three minutes of perfusion with modified Tyrodes buffer using a Zeiss AxioCam with Slidebook 4.0 (Intelligent Imaging Innovations, Inc., Denver, Colo., USA). All experiments were performed at 37° C. Each image in FIG. 7B is representative of 2-3 experiments.

These data suggest that under physiologically relevant shear FXI promotes fibrin formation independent of FXIIa in the presence of cellular blood components.

Inhibition of FXI with aXIMab.

Figure 8A:
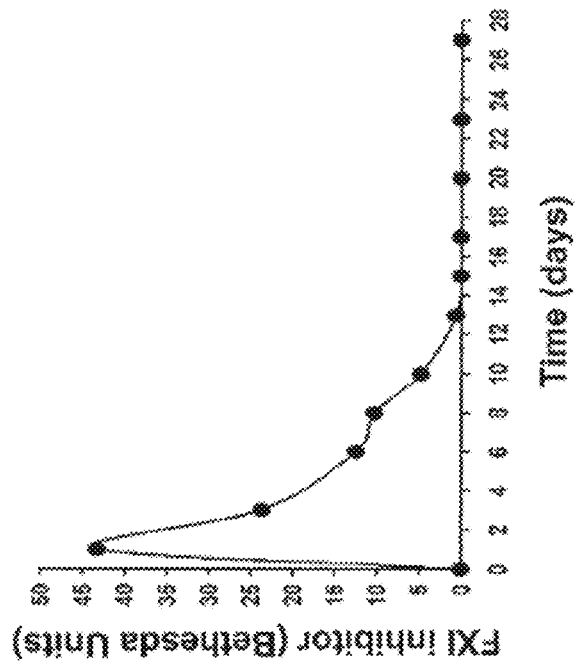
FIGS. 8A-8C. Inhibition of FXI procoagulant activity after administration of aXIMab. A single intravenous bolus of aXIMab (2 mg/kg) was given over 5 min to a single baboon. Plasma samples were collected into citrate anticoagulant and tested for (FIG. 8A) FXI procoagulant activity, FXI antigen (FXI:Ag), and (FIG. 8B) inhibitor levels over 4 weeks, with each time point being the mean of duplicate measurements. The FXI:Ag ELISA was able to detect both free and complexed FXI. Since the Bethesda assay detected only free FXI inhibitor (aXIMab), FXI:Ag and FXI activity at low inhibitor levels did not correlate until all complexes were cleared from circulation.
Figure 8B:
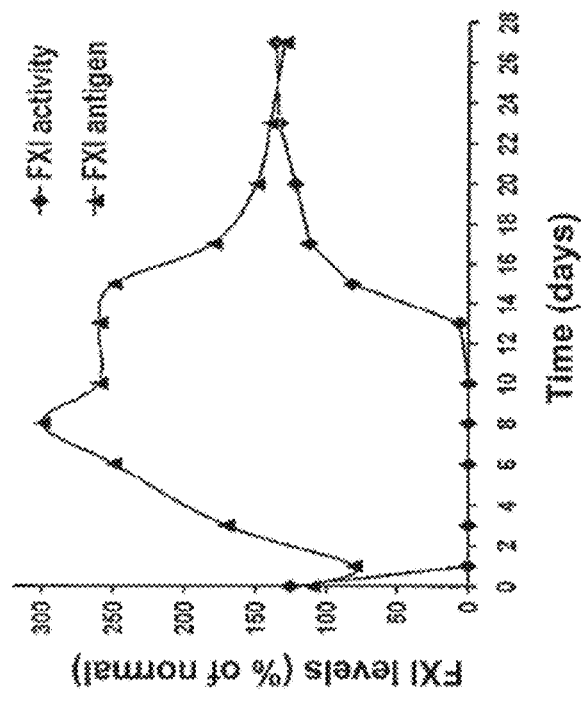
Figure 8C:
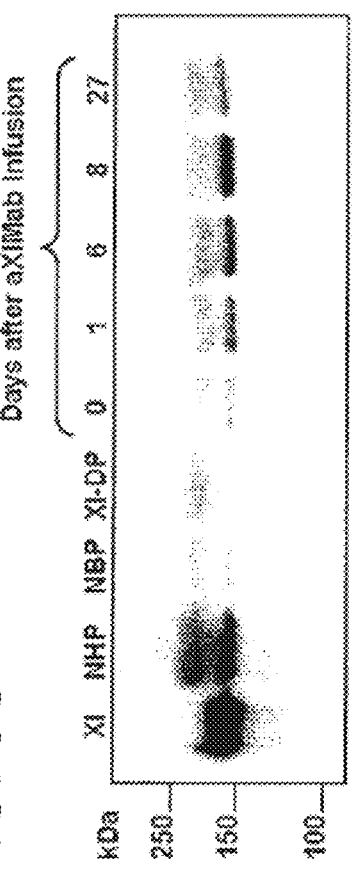

A baboon given aXIMab (1A6; 2 mg/kg) was followed for 4 weeks post-injection to assess FXI antigen (FXI:Ag), anticoagulant activity, and antibody inhibitor levels. FXI:Ag levels measured 1 h after aXIMab administration had decreased from 110% to 40% of NBP levels, but steadily increased thereafter, reaching 300% of control at day 8 post-infusion (FIG. 8A). Plasma FXI antigen remained above 200% of control through day 15, after which there was a decrease to 130% by day 27. FXI activity decreased from 125% to <1% 1 h after aXIMab administration, and remained inhibited by >99% for 10 days after administration. The FXI activity slowly climbed thereafter, normalizing to 136% by day 27. Maximum circulating FXI inhibitor levels were observed at 1 h post aXIMab infusion (72 Bethesda units [BU]), which decreased to <0.6 BU by day 15 (FIG. 8B). Consistent with the FXI:Ag ELISA data, the 160 kDa band representing the FXI homodimer on SDS PAGE and Western blots of plasma increased in intensity between day 0 and 8 (FIG. 8C). These results indicate that the anticoagulant effect of aXIMab was due to its sustained presence in the circulation, and its ability to block FXI activation and/or activity, and not to clearance of the enzyme from the plasma. Since aXIMab separates from FXI during SDS gel electrophoresis, it remains unclear whether inhibition of FXI by aXIMab caused a rebound effect (increase in FXI secretion) or the FXI-aXIMab immune complexes were slowly cleared from the circulation.

Figure 2:
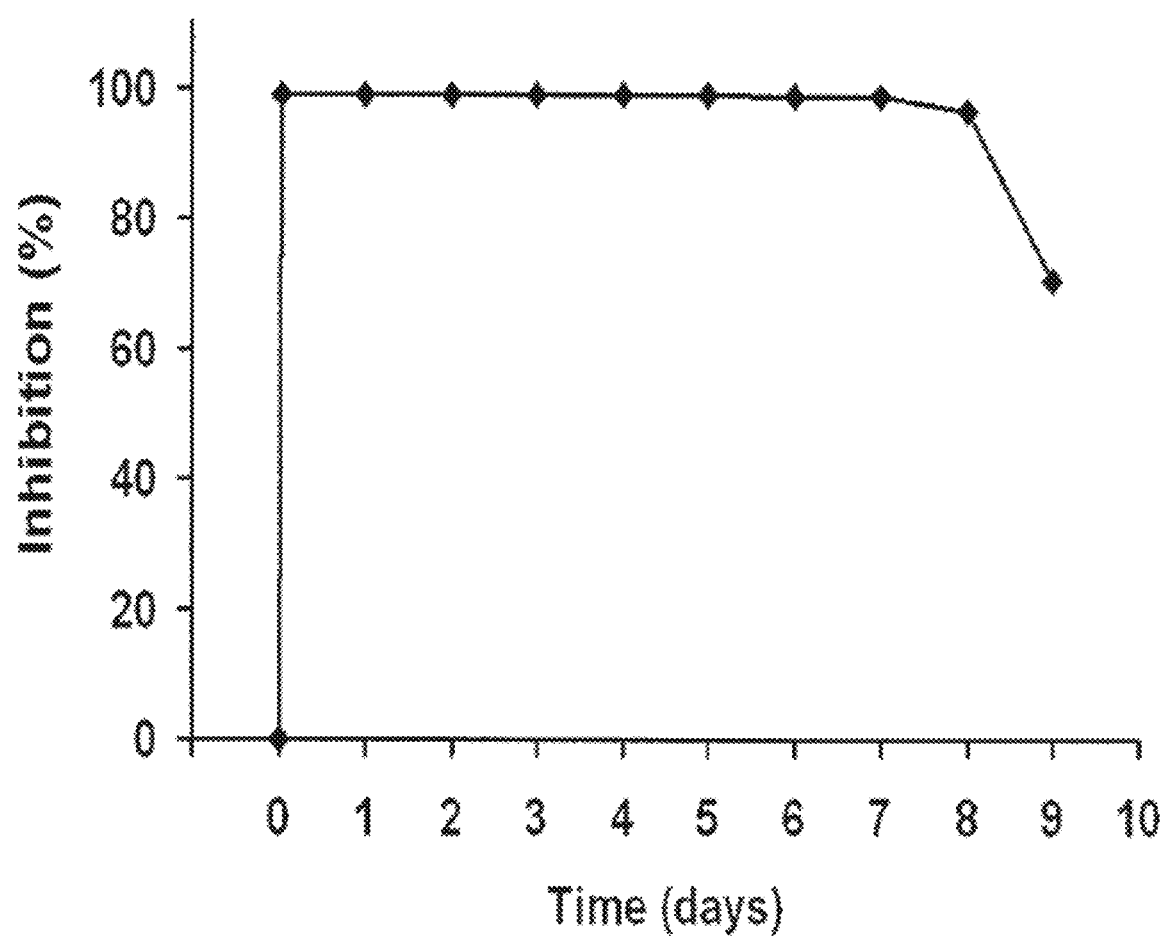
FIG. 2. Inhibition of the FXI procoagulant activity after administration of an anti-FXI monoclonal antibody (aXIMab). A single i.v. bolus (2 mg/kg) of aXIMab was given over 5 min to 4 separate baboons. Plasma samples were collected into $1/10^{th}$ v/v 3.2% citrate anticoagulant and tested in a one-stage clotting assay to assess the inhibition of FXI. Each time point represents the mean of 2-4 separate animals, with each exceeding 95% inhibition through day 8. All clotting times normalized by day 11.

Single i.v. bolus injections of aXIMab (2 mg/kg) were given to 4 baboons. The FXI procoagulant activity was inhibited by 99.0% (98.8-99.5%) at 1 hr after infusion and remained inhibited >95% in all animals for 8 days after administration (FIG. 2). No adverse reactions to the antibody were observed. aPTT measurements were prolonged after aXIMab administration to 65.6±2.0 sec compared with 30.5±0.7 sec in control animals, while the PT measurements were equivalent to PBS vehicle-treatment control values in the same animals (9.1±0.1 vs. 9.0±0.1 sec, respectively, n=11 for each treatment). Platelet aggregation in platelet rich plasma in response to adenosine diphosphate (ADP) and collagen was unchanged for aXIMab-treated animals versus control results.

aXIMab Treated Baboons are Protected from Collagen Initiated Thrombus Development.

Figure 3B:
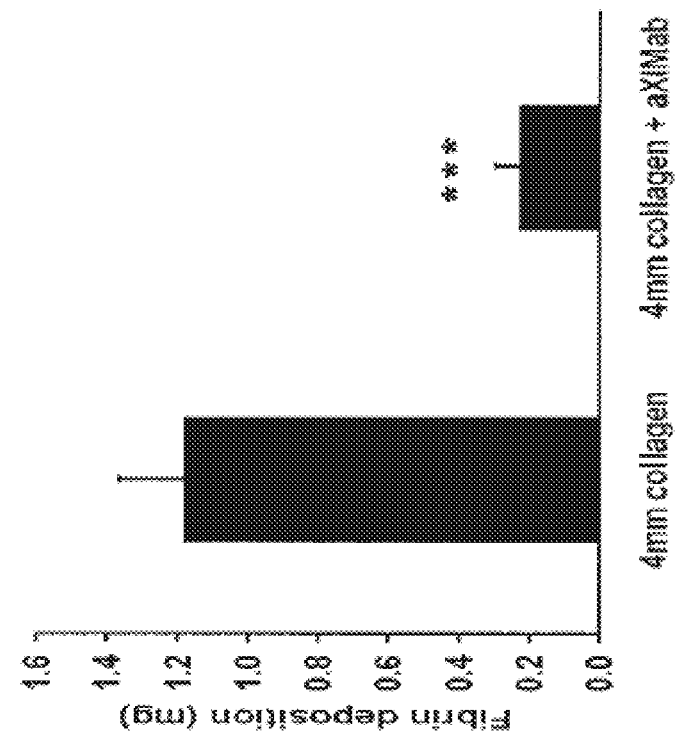
FIGS. 3A-3B. FXI inhibition reduces platelet and fibrin deposition on collagen coated vascular grafts. Effects of FXI inhibition on (FIG. 3A) platelet and (FIG. 3B) fibrin deposition on collagen coated (4 mm i.d.) vascular grafts. Thrombogenic grafts were placed in untreated (n=8) or aXIMab treated (n=6) animals (>95% FXI inhibition). Blood was allowed to flow through the devices at a clamped rate of 100 ml/min, producing an average wall shear rate of 265 s$^{-1}$. Significance levels are ***P=0.001. Values are means±SEM.
Figure 3A:
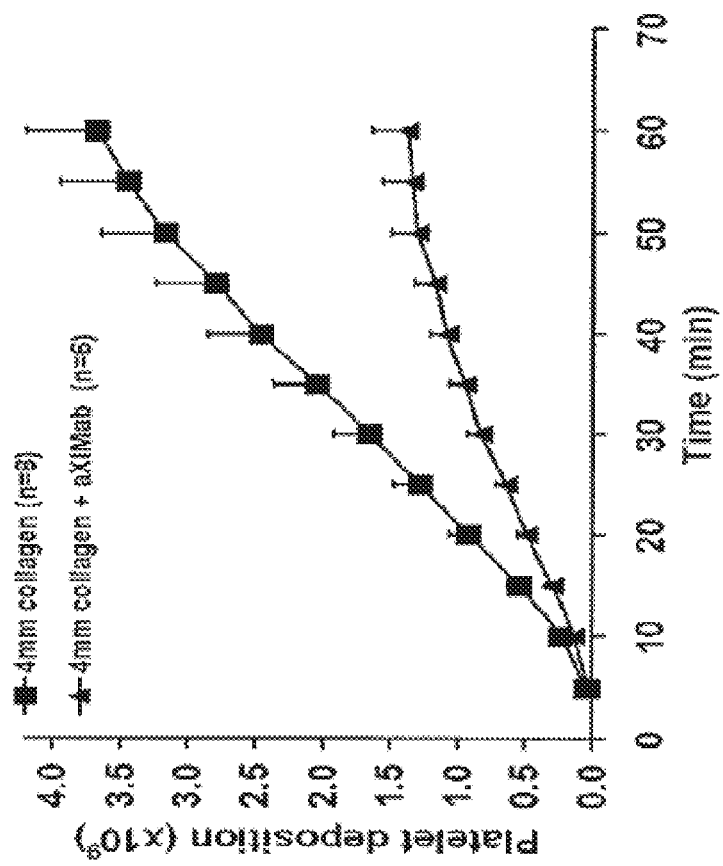

Previous studies have shown that FXI inhibition by a polyclonal antibody was antithrombotic on tissue factor and contact initiating surfaces in primates (Gruber & Hanson (2003) *Blood.* 102:953-955). Since vascular injury can also expose large amounts of platelet reactive collagen to flowing blood, the effect of FXI inhibition on collagen initiated thrombosis in baboons was examined. Significant differences in platelet accumulation between aXIMab- and vehicle-treated groups were seen as early as 10 min after graft exposure to blood flow (0.13±0.03×10$^9$ versus 0.23±0.03×10$^9$ platelets, aXIMab versus control, P<0.05). The differences remained statistically significant throughout the time course of thrombus propagation (FIG. 3A). Graft platelet accumulation at 60 min was 63% lower in aXIMab-treated animals than in vehicle controls (1.38±0.26×10$^9$ versus 3.68±0.52×10$^9$ platelets, aXIMab versus control, n=6 and 8, respectively, P<0.01; FIG. 3A). Systemic platelet counts prior to thrombosis studies were similar for both aXIMab and control groups (341±27×10$^3$/µl versus 337±31×10$^3$/µl, respectively), and did not change significantly following thrombosis experiments. End-point fibrin deposition was reduced by 81% compared with controls (0.23±0.07 mg and 1.18±0.19 mg, aXIMab versus control, P=0.001; FIG. 3B). Since aXIMab is monospecific for the A3 domain of FXI, these data verify that FXI plays an important role in thrombus propagation under arterial-type flow conditions in primates.

Reduced Thrombin Generation and Platelet Activation During FXI Inhibition.

Figure 4B:
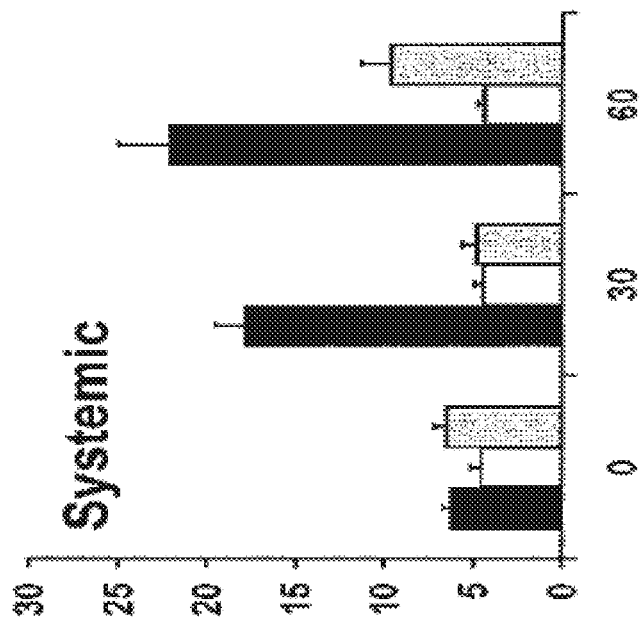
FIGS. 4A-4E. FXI inhibition by aXIMab reduces thrombin generation and platelet activation, while not affecting fibrinolysis.
Figure 4A:
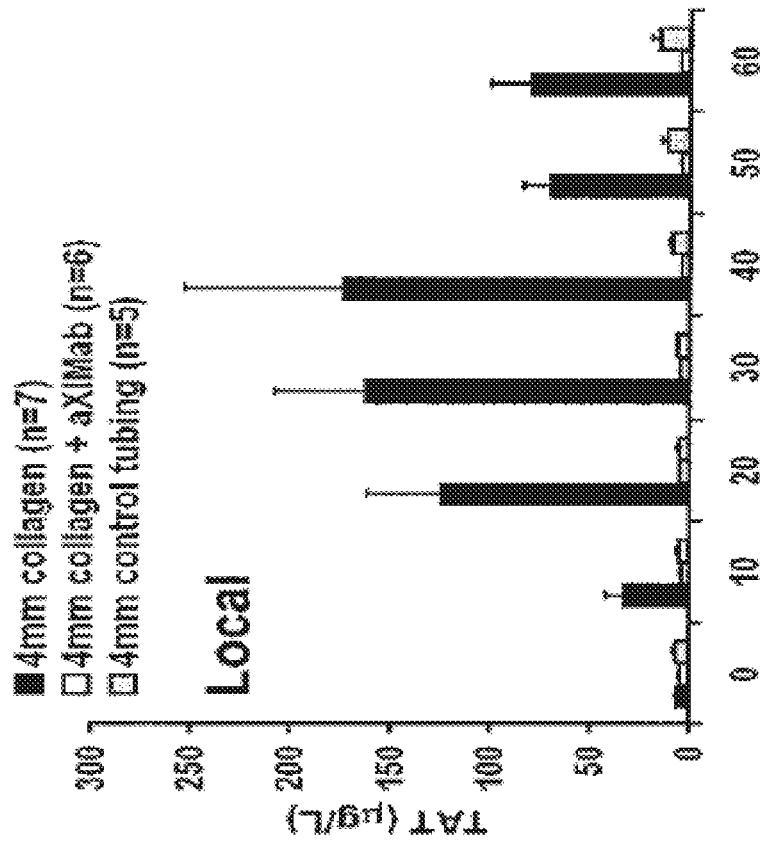
Figure 4D:
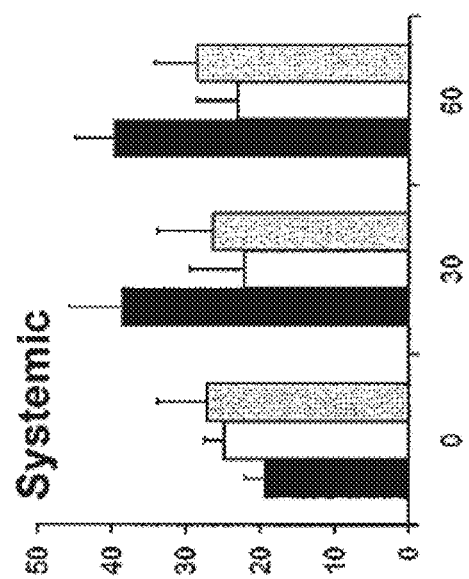
Figure 4C:
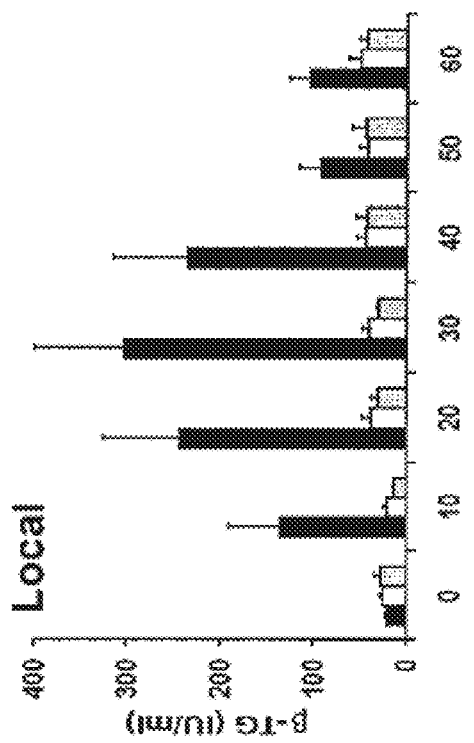
Figure 4E:
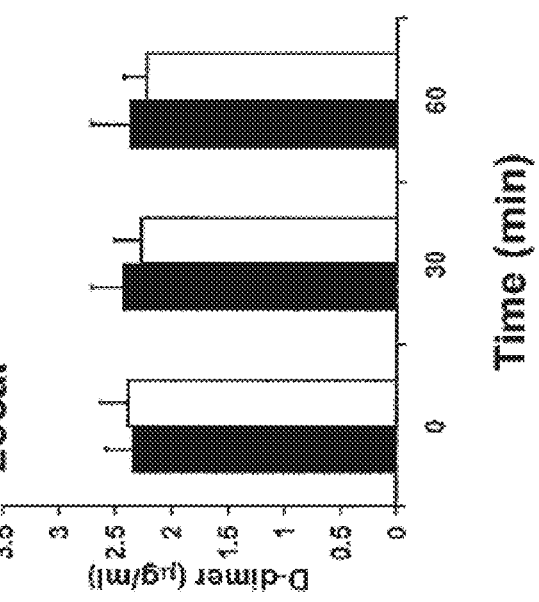

Since inhibition of FXI could reduce thrombus formation in vivo both by limiting thrombin-mediated platelet activation and fibrin formation and/or by increasing thrombolysis, levels of βTG, thrombin (TAT), and D-dimer were measured. Systemic pre-treatment βTG, TAT, and D-dimer levels were comparable in vehicle- and aXIMab-treated baboons (19.3±2.6 versus 24.8±3.8 IU/ml, 6.2±0.4 versus 4.6±0.6 µg/L, and 2.3±0.2 versus 2.4±0.2 µg/ml, respectively). Surprisingly, we observed a robust >20-fold increase in TAT release into the blood stream from the graft thrombus area, as measured in samples taken locally from the near-wall region, immediately downstream of thrombus formation in vehicle-treated baboons. Pre-treatment of baboons with aXIMab prevented the increase in local TAT levels, indicating a considerable reduction in thrombin generation in the absence of FXI activity (FIG. 4A). TAT levels in plasmas obtained by local sampling were reduced by up to 98% at 40 min, while systemic TAT levels were reduced by 81% at 60 min versus the untreated controls (4.3±0.5 versus 22.1±2.5 µg/L, n=6 and 7, respectively, P<0.001; FIG. 4B). Platelet activation at the thrombus surface, as assessed by the release of platelet α-granule βTG, was reduced by 86% at 30 min in samples taken distal to thrombi in aXIMab treated animals (FIG. 4C). Systemic βTG levels measured at 60 min were reduced by 42% by aXIMab (23.0±2.1 IU/ml, n=6) compared with vehicle-treated controls (39.5±5.5 IU/ml, n=7; FIG. 4D, P<0.05). Local D-dimer levels were not changed at 60 min compared with baseline systemic values in either control (2.3±0.2 and 2.4±0.4 µg/ml, respectively, n=7) or aXIMab treated animals (2.4±0.2 and 2.2±0.2 µg/ml, respectively n=6; FIG. 4E). Systemic D-dimer levels assessed at 60 min also were unchanged from baseline systemic values in both groups (2.4±0.3 and 2.3±0.2 µg/ml, control versus aXIMab treated animals). This confirms previous reports from similar baboon studies showing systemic D-dimer levels do not increase by 60 min after thrombus initiation, unless a thrombolytic agent is administered (Sundell et al. (1997) *Circulation* 96:941-948; Dichek et al. (1996) *Circulation* 93:301-309).

In order to assess the local sampling method for activation of coagulation and platelets, the system was tested without interposing a collagen coated thrombogenic device within the shunt loop. Although the tubing alone modestly increased the TAT and β-TG levels systemically and locally (FIG. 4A-C), the elevations were not statistically significant. No fibrin formation or platelet deposition was measured on the control tubing.

These data indicate that: 1) FXI plays an important role in thrombin generation and platelet activation during acute, arterial-type thrombus formation, and 2) endogenous local thrombolysis appears to be limited during the time course of these studies, regardless of FXI activity.

aXIMab Prevents Vascular Graft Occlusion.

Figure 5:
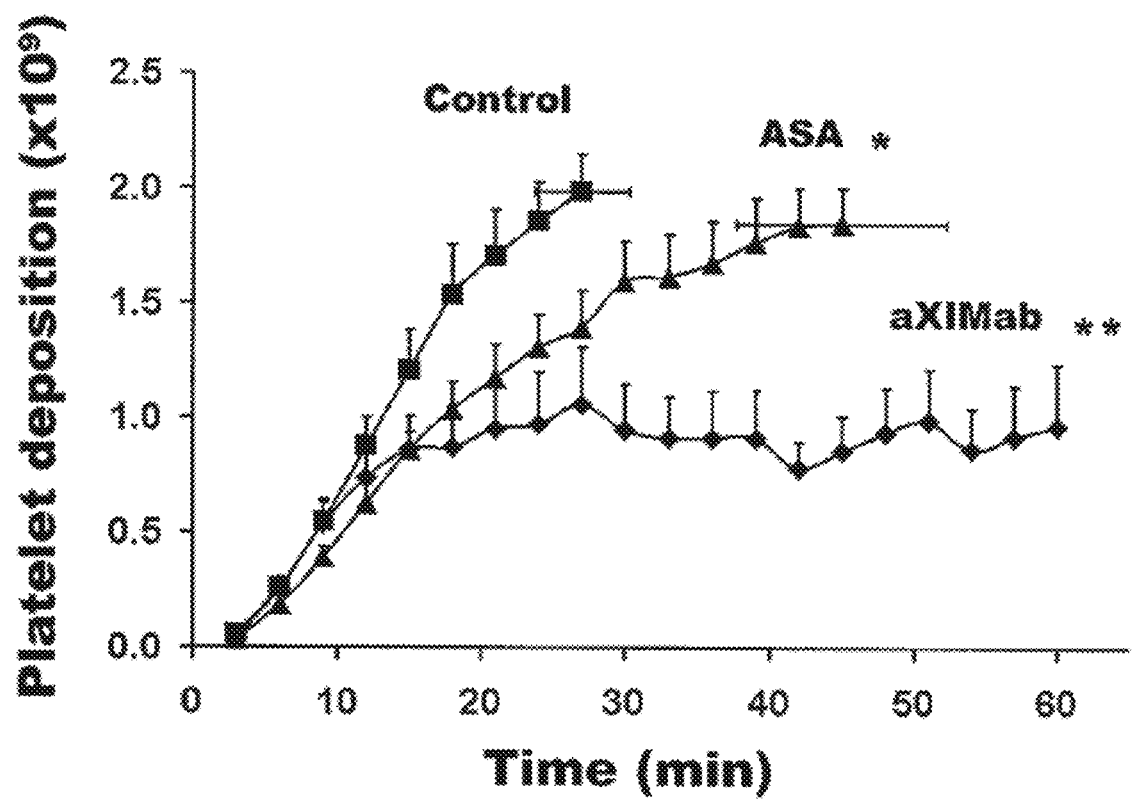
FIG. 5. FXI inhibition limits thrombus stability and prevents vascular graft occlusion under high arterial shear. Effects of FXI inhibition and ASA on platelet deposition on collagen coated (2 mm i.d.) vascular grafts are shown. Collagen-coated vascular graft segments were placed in permanent arterio-venous shunts in untreated (n=9), ASA treated (n=6), and aXIMab treated (n=5) animals. Blood was allowed to flow through the grafts at a rate of 100 ml/min, producing an average initial wall shear rate of 2120 s$^{-1}$. The flow was maintained by the pulsatile arterial pressure until the graft occluded (defined as ≤20 ml/min flow rate). Thrombi that formed in the grafts in the aXIMab treated animals were unstable and did not occlude the grafts during the 60 min-long studies. Significance levels are *P=0.05, **P<0.01 compared with non-treatment controls, using the log-rank test with the non-occluded devices being censored. Values are means±SEM.
Figure 6:
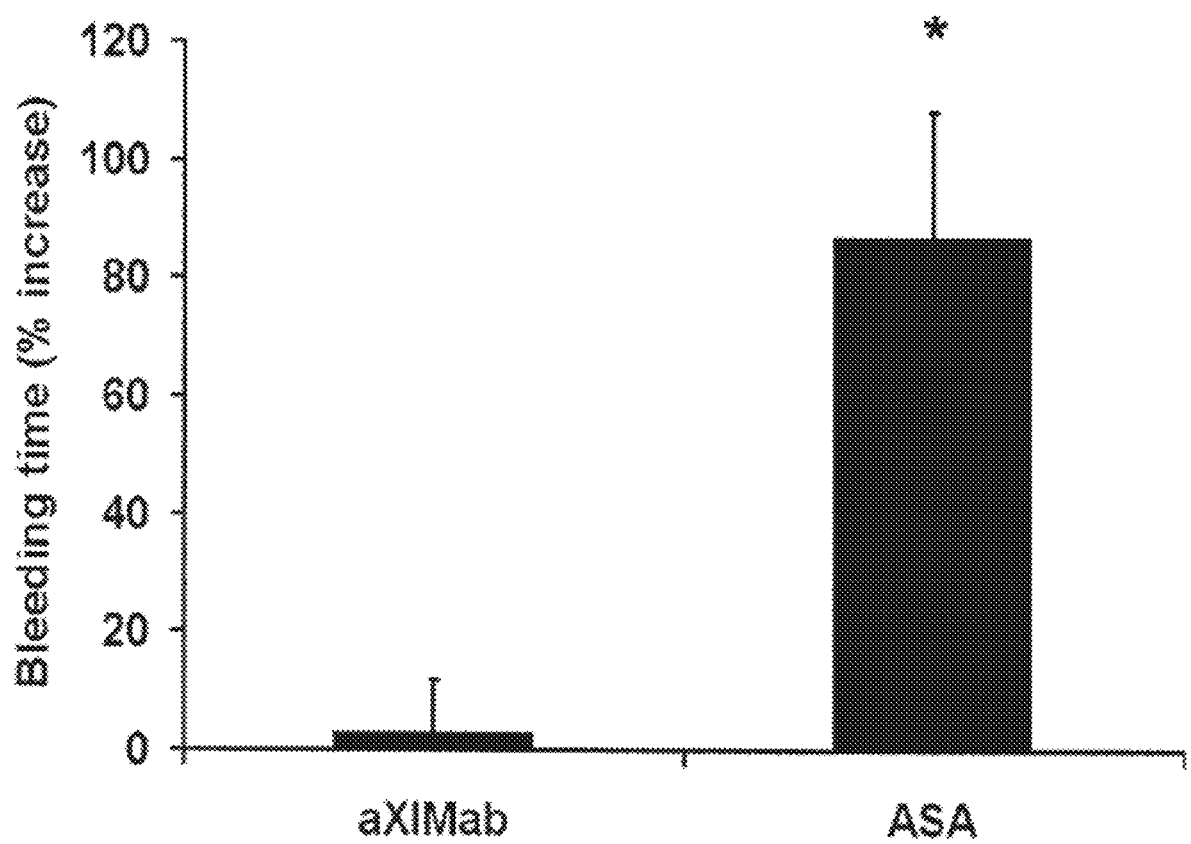
FIG. 6. Template bleeding time is normal in FXI inhibited baboons. Bleeding time was monitored repeatedly, on the volar surface of the lower arm, before and during treatment with aXIMab or ASA using an FDA-approved method and device (Surgicutt). ASA (n=10) prolonged the bleeding time while inhibition of FXI by aXIMab (n=18) did not demonstrably impair hemostasis compared with no treatment controls (n=14). The average of bleeding time changes are shown ±SEM. Significance levels are **P≤0.01.

Even though macroscopic thrombi formed rapidly in 4 mm i.d. vascular grafts, none of these grafts occluded during 60 min of blood perfusion. The effects of inhibiting FXI activity on thrombus formation and occlusion were therefore evaluated using smaller diameter (2 mm i.d.), collagen-coated vascular grafts that accumulated thrombus under higher shear conditions (wall shear rate=2120 $s^{-1}$). While the initial platelet accumulation rate was similar in aXIMab-treated and vehicle-treated baboons, thrombus stability was profoundly reduced in the absence of FXI activity. Within 12-15 min after initiation of blood perfusion the growth rate of platelet thrombus was reduced in all aXIMab-treated animals, and the number of platelets in the thrombus decreased abruptly, indicating reduced thrombus stability and net losses of thrombus material to embolization (FIG. 5). Treatment with aXIMab prevented graft occlusion over 60 min in all experiments (5 of 5 grafts remained patent), compared with the results in vehicle-treated controls in which 8 of 9 grafts occluded by 27.0±3.3 min (P<0.01; FIG. 5 and Table 1). Fibrin accumulation was also reduced by aXIMab treatment versus the vehicle-treated controls (0.18±0.02 versus 0.30±0.04 mg, respectively, P<0.01; Table 1). As expected, treatment with the positive antithrombotic control, high dose ASA, reduced platelet deposition in the 2 mm id. grafts, but did not completely interrupt occlusive thrombus formation. The time to graft occlusion was prolonged by aspirin by an average of 18 min in 4 grafts, while 2 additional grafts remained patent throughout the 60 min study interval. High dose ASA was therefore less effective in preventing graft occlusion than aXIMab (P<0.05, aXIMab versus ASA). These data indicate that FXI plays an important role in the thrombogenic process that leads to acute occlusion of small caliber vascular grafts.

TABLE 1

FXI inhibition by aXIMab prevents vascular graft occlusion in baboons.

| | Number occluded | Embolic events per experiment | Fibrin deposition (mg) |
|---|---|---|---|
| Control | 8/9 | n.d. | 0.30 ± 0.04 |
| ASA | 4/6 | 1.5 ± 0.6 | 0.23 ± 0.04 |
| aXIMab | 0/5 | 6.6 ± 0.9 | 0.18 ± 0.02* |

Data shown are absolute values or means ± SEM when applicable.
FXI, factor XI; aXIMab, anti-FXI monoclonal antibody; ASA, aspirin; n.d., none detected.
*P < 0.01 compared with control using the two-tailed Student's t-test.

No Antihemostatic Effects of FXI Inhibition with aXIMab.

Since all FDA approved anticoagulant and antiplatelet drugs produce unwanted antihemostatic effects, a new thrombosis specific therapy could provide a safe alternative for patients at a high risk of bleeding. The template bleeding is prolonged by both anti-platelet agents and anticoagulants in baboons (Gruber et al. (2007) *Blood* 109:3733-3740; Hanson et al. (1988) *J. Clin. Invest.* 81:149-158), yet FXI inhibition by aXIMab had no effect on the standard template bleeding time compared with vehicle-treated controls (3.5±0.3 versus 3.4±0.2 min, n=18 and 14, respectively). For comparison, single-dose ASA pre-treatment nearly doubled the bleeding time to 6.4±0.7 min (n=10, P<0.01). No re-bleeding phenomena, petechiae, hematomas or other adverse bleeding events were noted in any of the aXIMab- or ASA-treated animals during one week follow-up periods of observation. Taken together, these results show that inhibition of FXI activity by a neutralizing monoclonal antibody more effectively reduces acute occlusive arterial-type thrombus propagation, with less effect on primary hemostasis, than an antihemostatic dose of aspirin in baboons.

Discussion

These studies demonstrate that FXI is crucial for the facilitated production of robust amounts of thrombin on the flow surface of collagen initiated and propagating thrombi, which leads to platelet activation, fibrin formation, and thrombus stability under high and low arterial flow conditions. The antithrombotic/antiocclusive outcome of FXI inhibition was produced primarily through a substantial decrease in thrombin production rather than through an increase in fibrinolytic pathways. While not wishing to be bound by theory, since thrombin is the most potent physiological agonist of platelets, it is likely that the significant decrease in platelet activation observed during FXI inhibition resulted from the down regulation of thrombin generation. While FXI inhibition delayed platelet deposition onto collagen under low arterial flow, early thrombus growth at high flow mirrored that of control studies. These results are consistent with the increased efficiency of platelet GPIb binding to vWF on exposed collagen under high shear (Nishiya et al. (2002) *Blood.* 100:136-142), which produces less reliance on fibrin for early thrombus growth than under low shear conditions. In the propagation phase of thrombus growth however, the stability of thrombi exposed to high shear flow was robustly dependent on FXI and its ability to facilitate fibrin production and platelet activation. Indeed, under high arterial flow, enhanced distal thromboembolization was distinctly noted, which completely prevented vascular graft occlusion in all aXIMab treated animals. These findings are consistent with the antithrombotic and antiocclusive phenotype observed in FXI deficient mice following ferric chloride-induced arterial injury and thrombosis (Rosen et al. (2002) *Thromb. Haemost.* 87:774-776; Wang et al. (2005) *J. Thromb. Haemost.* 3:695-702; Wang el al. *J. Thromb. Haemost.* 4:1982-1988). However, none of the previous in vivo studies of flow-dependent thrombogenesis have provided evidence for the underlying antithrombotic mechanism of FXI inhibition.

FXI promotes clot resistance to fibrinolysis through thrombin-mediated activation of the metaloproteinase TAFI, which proteolytically modifies fibrin making it resistant to plasmin (Bajzar et al. (1996) *J. Biol. Chem.* 271:16,603-16,608; Broze & Higuchi (1996) *Blood* 88:3815-3823). In addition, inhibition of thrombin generation by anticoagulants enhances clot lysis due to a slower forming, less dense fibrin network (Gruber et al. (1994) *Blood* 83:2541-2548; Nenci et al. (1992) *Blood Coagul. Fibrinolysis* 3:279-285). Both processes may account, at least in part, for the enhanced lysis of blood clots formed in the presence of an anticoagulant anti-factor XI antibody in the clamped jugular vein of rabbits (Minnema et al. (1988) *J. Clin. Invest.* 101:10-14). During the present studies in baboons, the fibrinolytic degradation product D-dimer was measured by local blood sampling in the vicinity of fibrin, platelet, and leukocyte rich arterial-type thrombi (Gruber et al. (2007) *Blood* 109:3733-3740). Unlike TAT and βTG levels, there were no changes detected in local D-dimer for vehicle- or aXIMab-treated baboons. This finding suggests that endogenous fibrinolysis may not be a dominant process on the surface of thrombi during acute arterial thrombogenesis, which is consistent with the observation that TAFI deficient mice that were expected to have a fibrinolytic phenotype were not protected against injury-induced arterial thrombus formation (Nagashima et al. (2002) *J. Clin. Invest.* 109:101-110). Although the present study did not demonstrate a role for fibrinolysis in rapid thrombus development, more effective endogenous fibrinolysis in the absence of FXI activity may play a role in later stages of thrombus development and reorganization.

The dramatic reduction in local TAT during FXI inhibition with aXIMab illustrates the importance of FXI in thrombin production on the surface of collagen initiated and propagating thrombi, which contributes directly to fibrin formation, platelet activation, and thrombus stability.

Since PPACK-thrombin cannot be detected in the enzyme immunoassay described above, all local TAT was generated on the thrombus flow surface or within the ~1 cm distance from the thrombus to the PPACK infusion port (minus the systemic contribution). A benefit of using PPACK over other anticoagulants is its ability to rapidly inhibit a number of active serine proteases of the coagulation pathway, including factor Xa, which, as a part of the prothrombinase complex on activated platelets can be shielded from other anticoagulants and continue to generate thrombin. PPACK can also inhibit FXIa and limit unwanted contact activation within the sampling syringe over the 10 min sampling intervals. Without PPACK infusion the local sampling port occluded within 20-30 min. Based on the CFD models employed, the majority of the infused PPACK was captured within the sampling syringe. The small amount of PPACK that escaped into systemic circulation did not affect the platelet or fibrin deposition onto the 4 mm collagen coated grafts compared with historical data. Also, the total infused PPACK, if given systemically, is an order of magnitude less than that previously shown to prolong clotting times in baboons (Hanson et al. (1988) *Proc. Natl. Acad. Sci. USA.* 85:3184-188).

The decrease in local TAT and β-TG levels approaching 60 min in the no treatment collagen studies correlated with a decrease in platelet accumulation rate. It is unknown what led to the pacification of thrombus growth and mediator production, but is possibly the result of activated protein C (APC) generation or the production of other coagulation inhibitors.

Another intriguing outcome from these experiments suggests that circulating tissue factor (TF), either through platelets or microparticles, does not appear to play a significant role in promoting thrombus development. Without wishing to be bound by theory, the formation of TF/FVIIa complex should support thrombin production and fibrin formation independent of the contact pathway, but inhibiting FXI significantly limits fibrin production on collagen. A likely scenario is that FXIa promotes robust feedback amplification of thrombin, which promotes fibrin formation and platelet activation independent of circulating TF (Gailani et al. (1991) *Science.* 253:909-912; Broze et al. (1993) *Thromb. Haemost.* 70:72-74; Gailani et al. (2001) *Blood.* 97:3117-3122; Yun et al. (2003) *J. Biol. Chem.* 48:48112-48119; Baglia et al. (2004) *J. Biol. Chem.* 279:49323-49329).

The activation of FXI by factor XIIa may also be an important process during collagen initiated thrombus development.

The decrease in local TAT formation during FXI inhibition in baboons, combined with more limited platelet and fibrin accumulation, illustrates the importance of continued FXI-dependent thrombin generation in the propagation of thrombi. FXI dependent thrombin generation could occur via continued FXI activation by FXIIa, thrombin, and/or autoactivation (Gailani & Broze (1991) *Science* 253:909-912; Broze & Gailani (1993) *Thromb. Haemost.* 70:72-74). Data appears to play an important role in experimental thrombosis in mice (Renne et al. (2005) *J. Exp. Med.* 202:271-281). However, the present in vitro flow chamber data presents a mechanism whereby FXI promotes thrombosis independent of FXIIa during shear flow conditions in the presence of blood cells. Although thrombin-mediated FXI activation in static plasma assays in vitro has been questioned (Pedicord et al. (2007) *PNAS USA* 104:12,855-12,860), our flow-augmented thrombosis model clearly demonstrates a FXII independent thrombogenic pathway for FXI.

Interestingly, while free FXI:Ag decreased to <1% for over a week following aXIMab injection, total FXI:Ag levels temporarily increased several-fold above baseline following the disappearance of FXI activity in the baboon circulation. Whether this increase was due to a longer half-life of the circulating immune complexes or upregulation of FXI synthesis and/or secretion remains to be explored.

The evolutionary role of FXI has been difficult to fully elucidate, but these and other studies support a hypothesis that FXI functions, in part, to promote hemostasis after transvascular injury, which can expose large amounts of collagen to flowing flood. In the absence of FXI, prohemostatic occlusive thrombi may fail to stabilize, leading to increased and potentially fatal blood loss. Since tissue factor dependent hemostatic processes dominate during most bleeding events, FXI likely plays a role only after surgery or trauma, which are the dominant clinical manifestations of severe FXI deficiency in human patients. Moreover, since FXI seems to have its central effect on the flow surface of propagating thrombi, and patients with FXI deficiency have a generally mild bleeding tendency, FXI appears to be a more thrombosis specific treatment strategy than other existing antithrombotic methods, which can produce serious bleeding events independent of major trauma or surgery.

Overall, the evidence presented above shows that FXI is critical for collagen induced thrombus propagation by promoting a considerable local increase in thrombin production, which in turn contributes to robust platelet activation and fibrin formation. FXI inhibition however does not interfere substantially with primary hemostasis. Thus, therapeutic FXI inhibition represents an exceptionally promising treatment strategy to limit thrombus growth and thrombotic vessel occlusion (i.e. stroke, heart attack, DVT), while at the same time providing unmatched hemostatic safety compared with other currently available antithrombotic agents.

Example 2. Binding of the 1A6 Monoclonal Antibody to Human Factor XI

Results from a Western Blot study corroborating that anti-factor XI monoclonal antibody 1A6 recognizes Factor XI in human and non-human primate plasma is shown in FIG. 7A.

Figure 10:
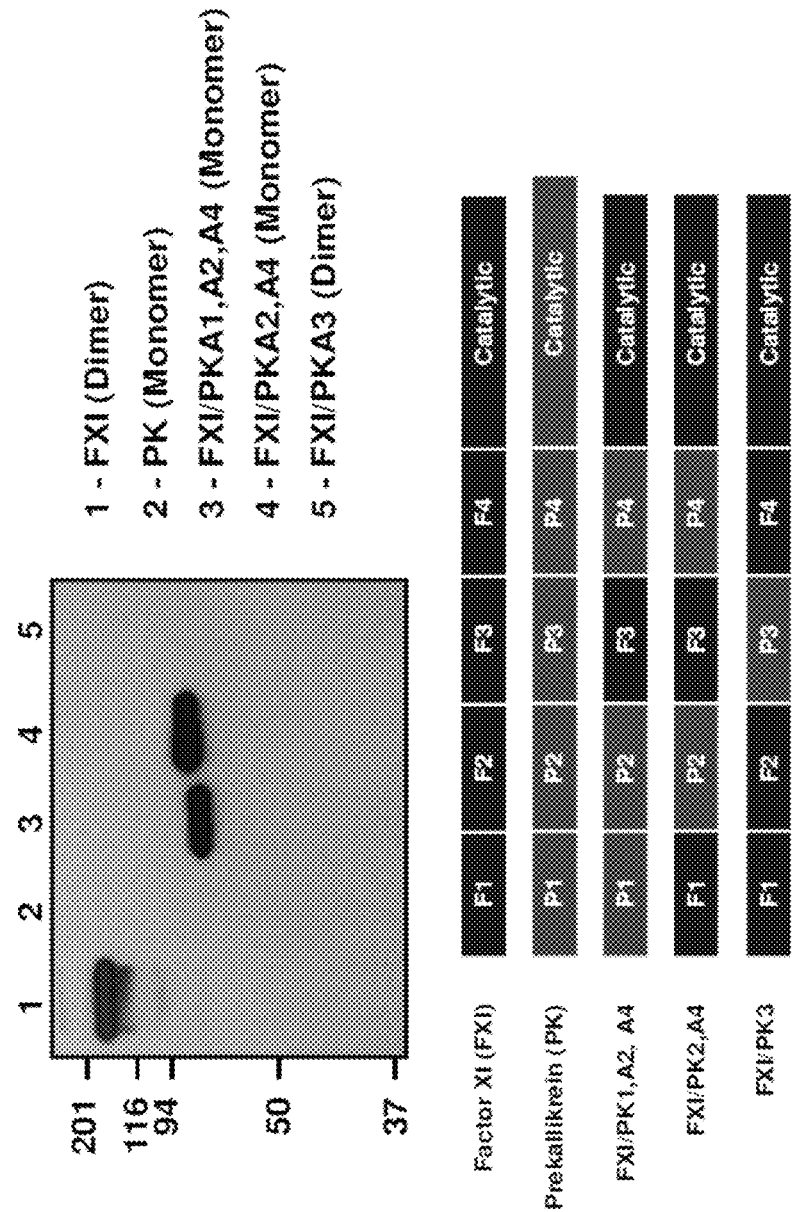
FIG. 10 shows Western Blots of the binding of anti-factor XI monoclonal antibody 1A6 to chimeric proteins of FXI and PK involving the substitution of PK domains with FXI domains. Monoclonal antibody 1A6 bound only to chimeras in which the A3 domain of FXI had been inserted.

Comparative binding studies for monoclonal antibody 1A6 were conducted using FXI, Prekallikrein (PK), and FXI/PK chimeras involving either the substitution FXI domains with PK domains (FIG. 9) or the substitution of PK domains with FXI domains (FIG. 10). As shown in the right panel of FIG. 9, monoclonal antibody 1A6 bound FXI but did not bind to PK. In addition, monoclonal antibody 1A6 bound all FXI/PK chimeras except the chimera in which the A3 domain of FXI was substituted with a PK domain (FIG. 9). For chimeras involving the substitution of PK domains with different FXI domains, antibody 1A6 was shown to bind only to chimeras in which the A3 domain of FXI had been inserted (FIG. 10). From these loss of function (FIG. 9) and gain of function (FIG. 10) studies, it was determined that monoclonal antibody 1A6 bound to an epitope on the FXI A3 domain.

Figure 11:
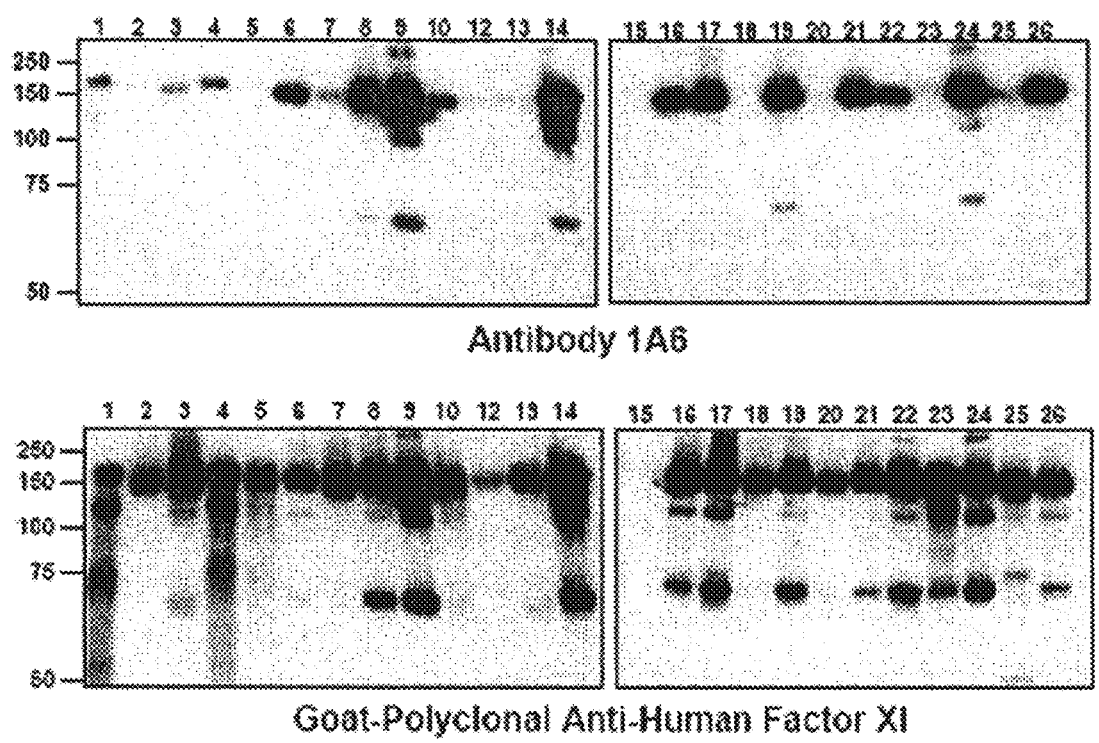
FIG. 11 shows Western Blots of the binding of anti-factor XI monoclonal antibody 1A6 to recombinant FXI proteins involving mutations of different amino acids within the A3 domain. Although a polyclonal anti-factor XI antibody bound to all FXI A3 domain mutants, monoclonal antibody 1A6 did not bind to some mutants in which amino acids within the A3 domain were substituted with Alanine.

Binding studies were also conducted using recombinant FXI proteins involving mutations of different amino acids within the A3 domain to determine amino acids important for the binding of monoclonal antibody 1A6. An example of the binding of monoclonal antibody 1A6 to a panel of 25 such recombinant proteins in which 2 or 3 adjacent amino acids within the A3 domain were replaced with Alanine is shown in FIG. 11. Although a polyclonal anti-factor XI antibody bound to all FXI A3 domain mutants, monoclonal antibody 1A6 did not bind to some mutants (see FIG. 11). Based on such studies, amino acids important for the binding of monoclonal antibody 1A6 to the FXI A3 domain were determined, and are shown in FIG. 12 (amino acids 183 to 197, 203 to 204, 234 to 236, 241 to 243, 252 to 254, and 258 to 260 of SEQ ID NO:1).

Example 3. Sequencing of the 1A6 Monoclonal Antibody and Coding Sequence mRNA was extracted from a hybridoma cell line expressing the murine antibody known as Aximab (1A6), reverse transcribed, and antibody specific transcripts were PCR amplified. PCR products were cloned for determination of the nucleotide and amino acid sequences of the heavy and light chain variable regions of this antibody.

The cell line was successfully recovered from frozen stocks. mRNA was extracted from the cell pellet of the hybridoma and RT/PCR was performed using a system of degenerate primer pools. Heavy chain variable region mRNA was amplified using a set of six degenerate primer pools (HA to HF) and light chain variable region mRNA was amplified using a set of eight degenerate primer pools (LA to LH).

Aximab Heavy Chain: A strong DNA band of approximately the expected size was observed in primer pool HD. DNA from this band was purified and cloned, and eight clones were sequenced. Four of these clones aligned to give a functional, rearranged heavy chain (Table 2, FIG. 13A).

TABLE 2

Aximab antibody (1A6) sequence analysis (CDR definitions and sequence numbering according to Kabat).

|  | H Chain | L Chain |
|---|---|---|
| CDR 1 Length | 7aa | 15aa |
| CDR 2 Length | 16aa | 7aa |
| CDR 3 Length | 14aa | 9aa |
| Closest Human Germline* | IGHV2-5 (76%) | IGKV4-1 (70%) |
| Closest Human FW1* | IGHV2-5 (80%) | IGKV4-1 (83%) |
| Closest Human FW2* | IGHV2-5 (86%) | IGKV4-1 (100%) |
| Closest Human FW3* | IGHV2-70 (72%) | IGKV3-11 (78%) |
| Closest Human J* | IGHJ6 (92%) | J4 (92%) |
| Max No. Mouse FR Residues** | 9 (2) | 5 (3) |

*Germline ID(s) indicated followed by % homology.
**Indicates maximum number of mouse residues that need to be sourced from human sequence segments with number of those potentially critical for affinity indicated in brackets.

Aximab Light Chain:

Strong DNA bands of the expected size were observed in primer pools LB, LC and LG. DNA from each band was purified and cloned, and four clones from each band were sequenced. The eight clones from pools LB and LC were found to align with the well described aberrant kappa transcript found in some hybridomas. The four clones from pool LG aligned to give a functional, rearranged light chain (Table 2, FIG. 13B).

The heavy and light chain variable region sequences from the Aximab hybridoma were determined. It was confirmed that Aximab is a murine IgG/kappa antibody and that both chains of this antibody have close sequence homologues in the human antibody databases through the framework regions (Table 2). This should facilitate subsequent humanization by either Composite Human Antibody™ technology or CDR-grafting. Heavy and light chain clones of each antibody were produced and are therefore available for humanization. Exemplary CDR-grafted heavy and light chain variable region sequences are shown in FIGS. 13C and 13D.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A method for inhibiting thrombosis without compromising hemostasis in a subject in need thereof, comprising administering to the subject a therapeutically effective dose of an anti-Factor XI (FXI) antibody or biologically active fragment thereof, wherein the antibody or biologically active fragment thereof comprises:
 a variable heavy ($V_H$) domain comprising three complementarity determining regions (CDRs), wherein the three CDRs comprise the three CDR sequences of SEQ ID NO: 3 or SEQ ID NO: 7; and a variable light (V$_L$) domain comprising three CDRs, wherein the three CDRs comprise the three CDR sequences of SEQ ID NO: 5 or SEQ ID NO: 9.

2. The method of claim 1, wherein at least one of the three CDRs of the V$_H$ domain comprises the amino acid sequence of SEQ ID NO: 10, SEQ ID NO: 11, or SEQ ID NO: 12.

3. The method of claim 2, wherein the three CDRs of the V$_H$ domain comprise the amino acid sequences of SEQ ID NO: 10, SEQ ID NO: 11, and SEQ ID NO: 12.

4. The method of claim 1, wherein at least one of the three CDRs of the V$_L$ domain comprises the amino acid sequence of SEQ ID NO: 13, SEQ ID NO: 14, or SEQ ID NO: 15.

5. The method of claim 4, wherein the three CDRs of the V$_L$ domain comprise the amino acid sequences of SEQ ID NO: 13, SEQ ID NO: 14, and SEQ ID NO: 15.

6. The method of claim 1, wherein the amino acid sequence of the V$_H$ domain is at least 90% identical to SEQ ID NO: 3 or SEQ ID NO: 7.

7. The method of claim 1, wherein the amino acid sequence of the V$_L$ domain is at least 90% identical to SEQ ID NO: 5 or SEQ ID NO: 9.

8. The method of claim 1, wherein the amino acid sequence of the V$_H$ domain comprises SEQ ID NO: 3 or SEQ ID NO: 7.

9. The method of claim 1, wherein the amino acid sequence of the V$_L$ domain comprises SEQ ID NO: 5 or SEQ ID NO: 9.

10. The method of claim 1, wherein the thrombosis is associated with myocardial infarction, unstable angina, atrial fibrillation, stroke, renal damage, pulmonary embolism, deep vein thrombosis, percutaneous translumenal coronary angioplasty, disseminated intravascular coagulation, sepsis, artificial organs, shunts, or prostheses.

11. The method of claim 1, further comprising administering the antibody in combination with an antithrombotic agent.

12. The method of claim 11, wherein the antithrombotic agent is a direct or indirect thrombin inhibitor, a Factor X inhibitor, a Factor IX inhibitor, a Factor XII inhibitor, a Factor V inhibitor, a Factor VIII inhibitor, a Factor XIII inhibitor, a Factor VII inhibitor, a tissue factor inhibitor, a profibrinolytic agent, a fibrinolytic or fibrinogenolytic agent, a carboxypeptidase B inhibitor, a platelet inhibitor, a selective platelet count reducing agent, or a Factor XI inhibitor.

13. The method of claim 1, wherein the subject is human.

14. The method of claim 1, wherein the antibody or biologically active fragment thereof is administered to the subject in a single dose of about 0.01 mg/kg to about 10 mg/kg.

15. The method of claim 14, wherein the antibody or biologically active fragment thereof is administered to the subject in a single dose of about 2 mg/kg.

16. The method of claim 1, wherein the antibody or biologically active fragment thereof is administered to the subject via systemic, topical, parenteral, or enteral administration.

17. A method for inhibiting thrombosis without compromising hemostasis in a subject in need thereof, comprising administering to the subject a therapeutically effective dose of a pharmaceutical composition, the pharmaceutical composition comprising a pharmaceutically acceptable carrier and an anti-Factor XI (FXI) antibody or biologically active fragment thereof, wherein the antibody or biologically active fragment thereof comprises:

a variable heavy (V$_H$) domain comprising three complementarity determining regions (CDRs), wherein the three CDRs comprise the three CDR sequences of SEQ ID NO: 3 or SEQ ID NO: 7; and a variable light (V$_L$) domain comprising three CDRs, wherein the three CDRs comprise the three CDR sequences of SEQ ID NO: 5 or SEQ ID NO: 9.

18. The method of claim 17, wherein the pharmaceutical composition is formulated for immediate release of the antibody or biologically active fragment thereof.

19. The method of claim 17, wherein the pharmaceutical composition is formulated for controlled release of the antibody or biologically active fragment thereof.

* * * * *